(12) United States Patent
Mechoulam et al.

(10) Patent No.: US 8,198,327 B2
(45) Date of Patent: Jun. 12, 2012

(54) FATTY ACID AMIDES AND USES THEREOF

(75) Inventors: Raphael Mechoulam, Jerusalem (IL); Itai Bab, Carmei Yossef (IL); Gary Milman, Maale Adumim (IL); Reem Smoum, Jerusalem (IL)

(73) Assignee: Yissum Research Development Company of the Hebrew University of Jerusalem, Ltd., Jerusalem (IL)

( * ) Notice: Subject to any disclaimer, the term of this patent is extended or adjusted under 35 U.S.C. 154(b) by 0 days.

(21) Appl. No.: 12/936,498

(22) PCT Filed: Apr. 7, 2009

(86) PCT No.: PCT/IL2009/000403
§ 371 (c)(1),
(2), (4) Date: Nov. 2, 2010

(87) PCT Pub. No.: WO2009/125409
PCT Pub. Date: Oct. 15, 2009

(65) Prior Publication Data
US 2011/0046222 A1  Feb. 24, 2011

Related U.S. Application Data

(60) Provisional application No. 61/043,483, filed on Apr. 9, 2008.

(51) Int. Cl.
*A61K 31/20* (2006.01)

(52) U.S. Cl. .............. 514/560; 514/558; 554/110

(58) Field of Classification Search .............. 514/558, 514/560; 554/110
See application file for complete search history.

(56) References Cited

U.S. PATENT DOCUMENTS

| | | | |
|---|---|---|---|
| 5,266,576 A | * | 11/1993 | Vincent et al. ............... 514/300 |
| 5,929,110 A | | 7/1999 | Nugent et al. |
| 2006/0014820 A1 | | 1/2006 | Burstein et al. |
| 2007/0276041 A1 | | 11/2007 | Oonuki et al. |

FOREIGN PATENT DOCUMENTS

| | | |
|---|---|---|
| CN | 1974545 A | 6/2007 |
| EP | 1 471 052 A1 | 10/2004 |
| EP | 1 867 994 A2 | 12/2007 |
| EP | 1867994 A2 * | 12/2007 |
| JP | 49-127918 A | 12/1974 |
| JP | 6-157284 A | 6/1994 |
| JP | 7-53488 A | 2/1995 |
| WO | 96/18600 A1 | 6/1996 |
| WO | 20081027533 A2 | 3/2008 |

OTHER PUBLICATIONS

Abe, et al., "TSH Is a Negative Regulator of Skeletal Remodeling", Cell, vol. 115, pp. 151-162, (2003).
Alexander, et al., "Human Parathyroid Hormone 1-34 Reverses Bone Loss in Ovariectomized Mice", Journal of Bone and Mineral Research, vol. 16, No. 9, pp. 1665-1673, (2001).

(Continued)

*Primary Examiner* — Deborah D Carr
(74) *Attorney, Agent, or Firm* — Vorys, Sater, Seymour and Pease LLP; Susanne M. Hopkins; Ari G. Zytcer

(57) ABSTRACT

Provided are fatty acid amides of amino acids, uses thereof and pharmaceutical compositions including them.

14 Claims, 12 Drawing Sheets

OTHER PUBLICATIONS

Allison, et al., "NPY and bone", NPY Family of Peptides in Neurobiology, Cardiovascular and Metabolic Disorders: from Genes to Therapeutics, pp. 171-182, (2006).

Bab, et al., "Review: Cannabinoid receptors and the regulation of bone mass", British Journal of Pharmacology, vol. 153, pp. 182-188, (2008).

Bab, "Regulation of Skeletal Remodeling by the Endocannabinoid System", Ann. N.Y. Acad. Sci., vol. 1116, pp. 414-422, (2007).

Bab, "The skeleton: stone bones and stoned heads?", Cannabinoids as Therapeutics, pp. 201-206, (2005).

Cascio, et al., "A structure-activity relationship study on N-arachidonoyl-amino acids as possible endogenous inhibitors of fatty acid amide hydrolase", Biochemical and Biophysical Research Communications, vol. 314, pp. 192-196, (2004).

Devane, et al., "Isolation and Structure of a Brain Constituent That Binds to the Cannabinoid Receptor", Science, vol. 258, pp. 1946-1949, (1992).

Elefteriou, et al., "Leptin regulation of bone resorption by the sympathetic nervous system and CART", Nature, vol. 434, pp. 514-520, (2005).

Idris, et al., "Regulation of bone mass, bone loss and osteoclast activity by cannabinoid receptors", Nature Medicine, vol. 11, No. 7, pp. 774-779, (2005).

Karsak, et al., "Cannabinoid receptor type 2 gene is associated with human osteoporosis", Human Molecular Genetics, vol. 14, No. 22, pp. 3389-3396, (2005).

Kim, et al., "Selective inhibition of Rank blocks osteoclast maturation and function and prevents bone loss in mice", The Journal of Clinical Investigation, vol. 119, No. 4, pp. 813-825, (2009).

Kondoh, et al., "Acyl Amino Acid Derivatives as Novel Inhibitors of Influenza Neuraminidase", Biosci. Biotech. Biochem., vol. 61, No. 5, pp. 870-874, (1997).

Lin, et al., "Review: NPY and Y receptors: lessons from transgenic and knockout models", Neuropeptides, vol. 38, pp. 189-200, (2004).

Mechoulam, et al., "Identification of an Endogenous 2-Monoglyceride, Present in Canine Gut, that Binds to Cannabinoid Receptors", Biochemical Pharmacology, vol. 50, No. 1, pp. 83-90, (1995).

Milman, et al., "N-arachidonoyl L-serine, an endocannabinoid-like brain constituent with vasodilatory properties", PNAS, vol. 103, No. 7, pp. 2428-2433, (2006).

Ofek, et al., "Peripheral cannabinoid receptor, CB2, regulates bone mass", PNAS, vol. 103, No. 3, pp. 696-701, (2006).

Patel, et al., "Review: The New Field of Neuroskeletal Biology", Calcif Tissue Int, vol. 80, pp. 337-347, (2007).

Robling, et al., "Biomechanical and Molecular Regulation of Bone Remodeling", Annu. Rev. Biomed. Eng., vol. 8, pp. 455-498, (2006).

Rosen, "BMP and BMP Inhibitors in Bone", Ann. N.Y. Acad. Sci., vol. 1068, pp. 19-25, (2006).

San Miguel, et al., "ERK1/2-activated de Novo Mapkapk2 Synthesis Is Essential for Osteogenic Growth Peptide Mitogenic Signaling in Osteoblastic Cells", The Journal of Biological Chemistry, vol. 280, No. 45, pp. 37495-37502, (2005).

Scutt, et al., "Laboratory Investigations: Cannabinoids Stimulate Fibroblastic Colony Formation by Bone Marrow Cells Indirectly via CB2 Receptors" Calcif Tissue Int, vol. 80, pp. 50-59, (2007).

Seto, et al., "Site of action of new antiviral amino acid analogs", Conference: Advan. Antimicrob. Antineoplastic Chemother., Proc. Int. Congr. Chemother., 7th (1972), Meeting Date 1971, vol. 1, Issue 1, 351-3. Editor(s): Hejzlar, Miroslay. Publisher: Univ. Park Press, Baltimore, MD. (Abstract).

Sun, et al., "FSH Directly Regulates Bone Mass", Cell, vol. 125, pp. 247-260, (2006).

Tabuchi, et al., "Inhibition of Octapeptide N-Myristoylation by Acyl Amino Acids and Acyl Alkanolamines", J. Enzyme Inhibition, vol. 12, pp. 27-36, (1997).

Takeda, et al., "Leptin Regulates Bone Formation via the Sympathetic Nervous System", Cell, vol. 111, pp. 305-317, (2002).

Tam, et al., "Involvement of Neuronal Cannabinoid Receptor CB1 in Regulation of Bone Mass and Bone Remodeling", Molecular Pharmacology, vol. 70, No. 3, pp. 786-792, (2006).

Tam, et al., "The cannabinoid CB1 receptor regulates bone formation by modulating adrenergic signaling", FASEB J., vol. 22, pp. 285-294, (2008).

Wasserman, et al., "Serratamolide, a Metabolic Product of Serratia", Communications to the Editor, Contribution No. 1670 from Harry H. Wasserman, et al., The Sterling Chemistry Laboratory, vol. 83, pp. 4107-4108; (1961).

* cited by examiner

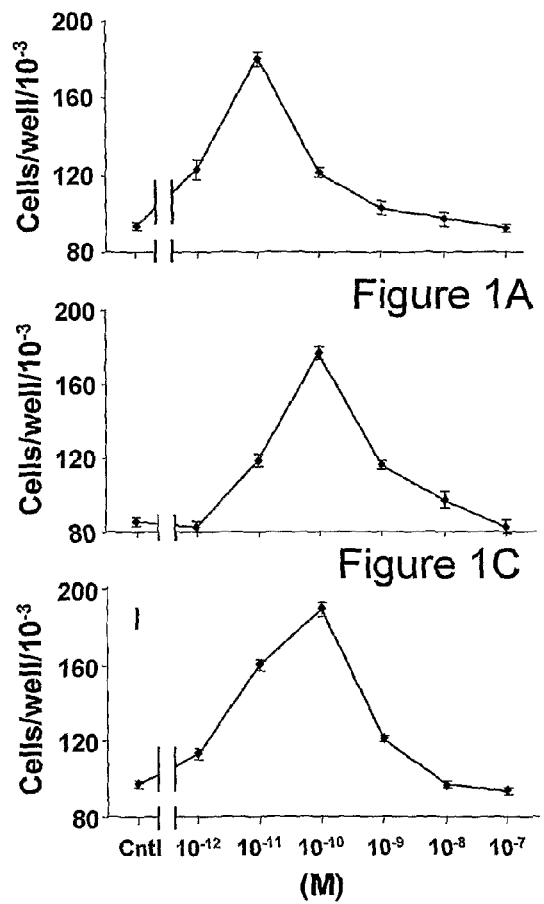
Figure 1A
Figure 1C
Figure 1E
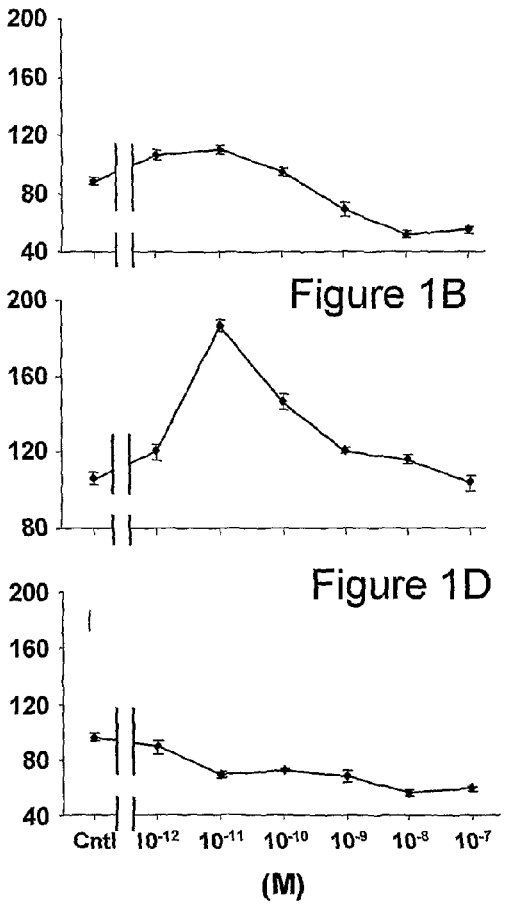
Figure 1B
Figure 1D
Figure 1F

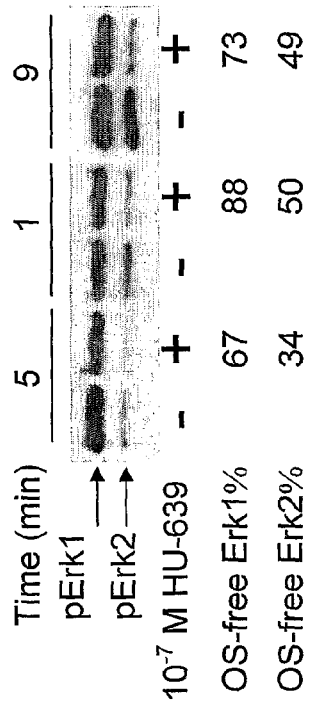
Figure 5E
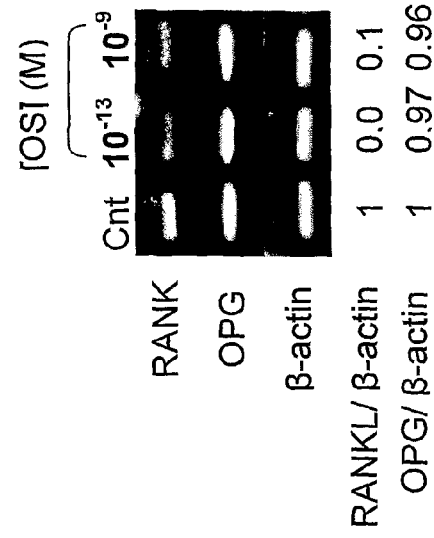
Figure 5F
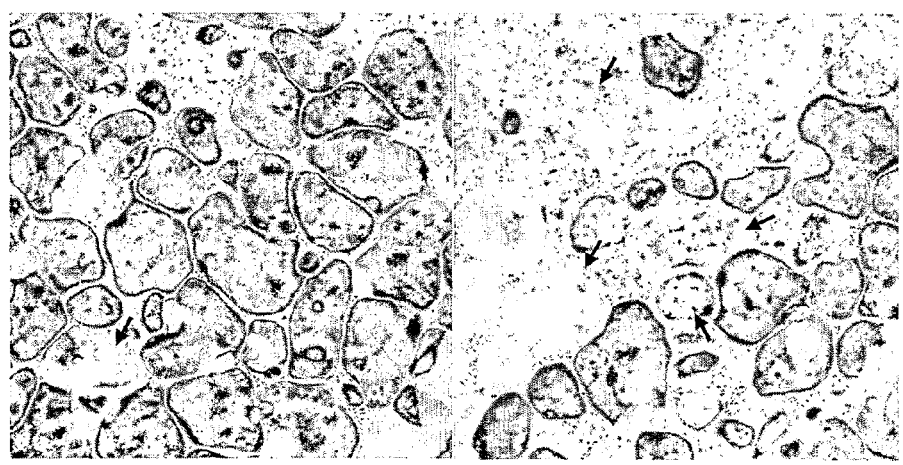
Figure 5C
Figure 5D

FATTY ACID AMIDES AND USES THEREOF

This is a National Phase Application filed under 35 U.S.C. 371 as a national stage of PCT/IL2009/000403, filed on Apr. 7, 2009, an application claiming the benefit under 35 U.S.C. 119(e) of U.S. Provisional Application No. 61/043,483, filed on Apr. 9, 2008, the contents of each of which are hereby incorporated by reference in their entirety.

FIELD OF THE INVENTION

This invention relates to fatty acid amides of amino acids, uses thereof and pharmaceutical compositions comprising them.

BACKGROUND OF THE INVENTION

In vertebrates, skeletal mass is determined by continuous remodeling consisting of the concerted and balanced action of osteoclasts, the bone resorbing cells, and osteoblasts, the bone forming cells. Osteoporosis, the most prevalent degenerative disease in developed countries, results from the impairment of this balance, leading to bone loss and increased fracture risk. Bone remodeling is regulated by a complex convergence of circulating hormones including sex steroids, parathyroid hormone and pituitary-derived thyroid and follicle stimulating hormones, on one hand, and local regulators of bone cell activity such as bone morphogenetic proteins, receptor activators of nuclear factor κB ligand (RANKL) and a number of cytokines, on the other hand [Abe et al, 2003; Sun et al, 2006; Rosen, 2006; Robling et al, 2006].

Recent work has shown that neuroendocrine pathways and neurotransmitters also have a key role in the regulation of bone remodeling [Takeda et al, 2002; Elefteriou et al, 2005; Lin et al, 2004; Allison and Herzog, 2006; Patel and Elefteriou, 2007; Tam et al, 2008]. Upon finding of a skeletal endocannabinoid system [Bab, 2005; Idris et al, 2005; Karsak et al, 2005; Ofek et al, 2006, Tam et al, 2006, Tam et al, 2008; Scutt and Williamson, 2007; Bab, 2007; Bab and Zimmer, 2008], it was particularly shown that arachidonoyl ethanolamide (anandamide, AEA) [Devane et al., 1992] and 2-archidonoylglycerol (2-AG) [Mechoulam et al, 1995] are present in bone tissue. Furthermore, N-arachidonoyl-serine (ARA-S), a mitogenically active compound, which is structurally related to endocannabinoids was identified in the brain [Milman et al, 2006].

There is a growing need in aging modern society for potent and stable compositions capable of promoting bone cell formation in order to achieve better treatment of medical conditions associated with bone tissue loss.

SUMMARY OF THE INVENTION

In one aspect of the present invention there is provided a fatty acid amide of an amino acid, including a stereoisomer and a salt thereof, wherein the fatty acid moiety is optionally substituted by at least one group selected from —$C_1$-$C_6$ alkyl, —OH, —SH and —$SR_2$; and the amino acid moiety is optionally substituted by at least one group selected from —$C_1$-$C_6$ alkyl, —OH and —$OR_3$; wherein each of $R_1$, $R_2$ and $R_3$ is independently —$C_1$-$C_6$ alkyl; provided that at least one of said fatty acid moiety and amino acid moiety is substituted.

As used herein the term "fatty acid amide of an amino acid" is meant to encompass the amide achieved upon conjugation of a fatty acid moiety and an amino acid moiety through the formation of an amidic bond. It should be understood that while compounds of the invention are generally referred to as a conjugates of a fatty acid moiety and an amino acid moiety, the conjugates of the invention may be formed from a great variety of precursors, employing a single or multi-step synthetic methodologies.

When referring to a "fatty acid moiety" it should be understood to encompass an acyl moiety derivable from a fatty acid, namely being generally of the form RC(=O)—, wherein R represents the aliphatic chain of the corresponding fatty acid, and wherein the point of attachment of the fatty acid moiety to the amino acid moiety of the fatty acid amide is through the carbonyl carbon atom of the fatty acid moiety.

As used herein the term "fatty acid" is meant to encompass a mono carboxylic acid having an aliphatic chain ("tail"), wherein said aliphatic chain may be either saturated, monounsaturated (having one unsaturated bond anywhere on the aliphatic chain) or poly unsaturated (having at least two unsaturated bonds anywhere on the aliphatic chain). An unsaturated bond on the aliphatic chain may be a double (in the cis and/or trans configuration) or a triple bond. The length of the aliphatic chain (being either saturated, monounsaturated or polyunsaturated) of a fatty acid may vary between 8 to 24 carbon atoms. Fatty acids may be derived from a natural source (either an animal or plant source), synthetic source or semi-synthetic source.

Non-limiting examples of saturated fatty acids are lauric acid, myristic acid, palmitic acid and stearic acid. Non-limiting examples of monounsaturated fatty acids are myristoleic acid, palmitoleic acid and oleic acid. Non-limiting examples of polyunsaturated fatty acids are linoleic acid, α-linolenic acid, arachidonic acid, eicosapentaenoic acid, erucic acid and docosahexaenoic acid.

In some embodiments, said fatty acid moiety of a fatty acid amide is selected from a saturated fatty acid moiety, a monounsaturated fatty acid moiety and a poly unsaturated fatty acid moiety. In other embodiments of the invention, the fatty acid moiety is an oleoyl fatty acid moiety ($CH_3(CH_2)_7CH$=$CH(CH_2)_7C$(=O)—), namely derived from the corresponding oleic acid.

In some further embodiments, said fatty acid moiety is substituted by at least one group selected from —$C_1$-$C_6$ alkyl, —OH, —$OR_1$, —SH and —$SR_2$, wherein $R_1$ and $R_2$ are each independently —$C_1$-$C_6$ alkyl. In other embodiments, said fatty acid moiety is substituted by at least one —$C_1$-$C_6$ alkyl. In yet other embodiments, said at least one $C_1$-$C_6$ alkyl is methyl.

In further embodiments, said at least one substitution is on at least one of the α- or β-positions of said fatty acid moiety. As known in the art, the "α-position of said fatty acid moiety" is the carbon atom on the aliphatic chain of the fatty acid moiety which is directly adjacent to the carbonyl carbon atom of the fatty acid moiety; the "β-position of said fatty acid moiety" is the carbon atom on the aliphatic chain of the fatty acid moiety which is the second carbon atom adjacent to the carbonyl carbon atom of the fatty acid moiety.

In some embodiments, a fatty acid amide of the invention is substituted at the α-position of the fatty acid moiety. In other embodiments, a fatty acid amide of the invention is substituted at the β-position of the fatty acid moiety. In further embodiments, a fatty acid amide of the invention is substituted at both the α- and β-positions of the fatty acid moiety.

When referring to an "amino acid moiety" it should be understood to encompass a radical derivable from an amino acid, namely being generally of the formula —NHCHR-COOH, wherein the point of attachment of said amino acid moiety to a fatty acid moiety, as defined herein, is through the amine of the amino acid moiety, as explained above.

The "amino acid" is an amino acid (i.e., alpha-amino acid or beta-amino acid) as known in the art. In some embodiments, the amino acid moiety is derived from an amino acid of the general formula $H_2NCHRCOOH$, wherein R is an organic substituent. Non-limiting examples of amino acids are alanine, asparagine, aspartate, cysteine, glutamate, glutamine, glycine; proline, serine, tyrosine, arginine, histidine, isoleucine, leucine, lysine, methionine, phenylalanine, threonine, tryptophan, and valine. An amino acid as used herein may be derived from of a natural source, synthetic or semi-synthetic source. An amino acid as used herein may also be in the D- or L-configuration. In some embodiments, an amino acid is an L-amino acid.

In some embodiments, said amino acid moiety is selected from serine, cysteine, tyrosine and phenylalanine. In other embodiments, said amino acid moiety is serine.

In some embodiments, of the invention said fatty acid moiety is optionally substituted by one group selected from —$C_1$-$C_6$ alkyl, —OH, —SH and —$SR_2$; and the amino acid moiety is optionally substituted by one group selected from —$C_1$-$C_6$ alkyl, —OH and —$OR_3$; wherein each of $R_1$, $R_2$, and $R_3$ is independently —$C_1$-$C_6$ alkyl; provided that at least one of said fatty acid moiety and amino acid moiety is substituted.

In further embodiments, said amino acid moiety is unsubstituted.

In still further embodiments, said amino acid moiety is substituted by at least one group selected from —$C_1$-$C_6$ alkyl, —OH, and —$OR_3$, wherein $R_3$ is —$C_1$-$C_6$ alkyl. In other embodiments, said amino acid is substituted by —$C_1$-$C_6$ alkyl. In further embodiments, said —$C_1$-$C_6$ alkyl is methyl. In yet additional embodiments, said substitution is on the α-position of said amino acid moiety.

The "α-position of said amino acid moiety" is the carbon atom on the amino acid moiety which is directly adjacent to the carbonyl carbon atom of the amino acid moiety.

The expression "provided that at least one of said fatty acid moiety and amino acid moiety is substituted" relates to the fact that at least one of a fatty acid moiety and an amino acid moiety of the fatty acid amide of the invention is substituted as defined herein.

In some embodiments, said amino acid moiety is substituted by at least one substituent. In other embodiments, said substitution on said amino acid moiety is on the α-position of the amino acid moiety.

In other embodiments, said fatty acid moiety is substituted by at least one substituent. In further embodiments, said at least one substitution on the fatty acid moiety is on the α and/or β-position of the fatty acid moiety. In yet further embodiments each of said amino acid and fatty acid moieties is substituted by at least one substituent. It should be noted that each substituent either on fatty acid moiety and/or amino acid moiety is independently selected as defined herein.

The term "stereoisomer" as used herein is meant to encompass an isomer that possess identical constitution as a corresponding stereoisomer, but which differs in the arrangement of its atoms in space from the corresponding stereoisomer. For example, stereoisomers may be enantiomers, diastereomers and/or cis-trans (E/Z) isomers. It should be understood that a composition comprising a fatty acid amide of the invention may comprise single enantiomers, single diastereomers as well as mixtures thereof at any ratio (for example racemic mixtures, non racemic mixtures, mixtures of at least two diastereomers and so forth). Furthermore, the invention encompasses any stereoisomer of a fatty acid amide of the invention achieved through in vivo or in vitro metabolism, or by any type of synthetic rout.

The term "salt" as used herein is meant to encompass any salt achieved by acid or base addition. In some embodiments, the salt is an acid addition salt obtained by protonation of a fatty acid amide of the invention (for example at the amidic moiety). In other embodiments, the salt is a base addition salt obtained by deprotonation of a proton from the fatty acid amide of the invention (for example from the acidic moiety, i.e. —COOH of the fatty acid amide). Counter ion forming a salt of a fatty acid amide of the invention can, in a non-limiting fashion, include inorganic or organic cations, which in some embodiments are pharmaceutically acceptable, such as alkaline metal cations e.g. potassium or sodium cation, alkaline earth metal cations such as magnesium or calcium, or ammonium cation including e.g. the cations derived from an organic nitrogen-containing base, such as trialkylamine-derived cations for example triethylammonium ion.

In some embodiments of the invention, a fatty acid amide, a stereoisomer or a salt thereof, is a compound of general formula (I):

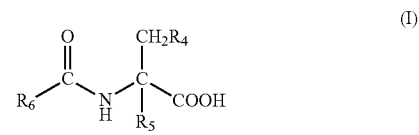

(I)

wherein $R_4$ is independently selected from —OH, —SH, phenyl and hydroxyl phenyl; $R_5$ is independently selected from H, —$C_1$-$C_6$ alkyl, —OH and —$OR_3$; $R_6$ is independently selected from —$C_{13}$-$C_{22}$ alkyl, —$C_{13}$-$C_{22}$ alkenyl and —$C_{13}$-$C_{22}$ alkynyl; $R_6$ being optionally substituted by at least one group selected from —$C_1$-$C_6$ alkyl, —OH, —$OR_1$, —SH and —$SR_2$; wherein each of $R_1$, $R_2$, and $R_3$ is independently —$C_1$-$C_6$ alkyl; and provided that when $R_5$ is hydrogen $R_6$ is substituted.

The term "alkyl" is meant to encompass a monovalent linear (unbranched), branched or cyclic saturated hydrocarbon radical. When referring to "$C_1$-$C_6$ alkyl" it should be understood to encompass any linear or branched alkyl having 1, 2, 3, 4, 5, or 6 carbon atoms. Non-limiting examples of $C_1$-$C_6$ alkyl include methyl, ethyl, n-propyl, iso-propyl, n-butyl, 2-butyl, 3-butyl, n-isobutyl, 2-isobutyl, n-pentyl, 2-pentyl, 3-pentyl, 2-methylbutyl, 2-dimethylpropyl, n-hexyl, 2-hexyl, 3-hexyl, 2-methylpentyl, 3-methylpentyl, 2,3-dimethylbutyl, 2,2-dimethylbutyl, 2-methyl-2-ethyl-propyl, cyclobutyl, 1-methyl-clyclobutyl, 2-methyl-cyclobutyl, 1,1-dimethyl-cyclobutyl, 1,2-dimethyl-cyclobutyl, 2,2-dimethyl-cyclobutyl, methyl-1-cyclobutyl, 1-cyclobutyl-ethyl, 2-cyclobutyl-ethyl, cyclopentyl, 1-methyl-cyclopentyl, 2-methyl-cyclopentyl. Similarly, when referring to "—$C_{11}$-$C_{20}$ alkyl" it should be understood to encompass any linear or branched alkyl radical having 11, 12, 13, 14, 15, 16, 17, 18, 19, 20 carbon atoms. Similarly, when referring to "—$C_{13}$-$C_{22}$ alkyl" it should be understood to encompass any linear or branched alkyl radical having 13, 14, 15, 16, 17, 18, 19, 20, 21, 22 carbon atoms.

The term "alkenyl" is meant to encompass a linear (unbranched) or branched hydrocarbon chain having at least one double bond. A double bond may be between any two carbon atoms of the alkenyl chain and may be in the cis or trans (or the E or Z) configuration. A double bond of an alkenyl may be unconjugated or conjugated to another unsaturated group. When referring to "—$C_{13}$-$C_{22}$ alkenyl" it should be understood to encompass any linear or branched alkenyl radical having 13, 14, 15, 16, 17, 18, 19, 20, 21, 22 carbon atoms.

Similarly, when referring to "—$C_{11}$-$C_{20}$ alkenyl" it should be understood to encompass any linear or branched alkenyl radical having 11, 12, 13, 14, 15, 16, 17, 18, 19, 20 carbon atoms.

The term "alkynyl" is meant to encompass a linear (unbranched) or branched hydrocarbon chain having at least one triple bond. The triple bond may be between any two carbon atoms of the alkynyl chain. The triple bond of an alkynyl may be unconjugated or conjugated to another unsaturated group. When referring to "—$C_{13}$-$C_{22}$ alkynyl" it should be understood to encompass any linear or branched alkynyl radical having 13, 14, 15, 16, 17, 18, 19, 20, 21, 22 carbon atoms. Similarly, when referring to "—$C_{11}$-$C_{20}$ alkynyl" it should be understood to encompass any linear or branched alkynyl radical having 11, 12, 13, 14, 15, 16, 17, 18, 19, 20 carbon atoms.

The term "phenyl" is meant to encompass a —$C_6H_5$ ring radical.

The term "hydroxyl phenyl" is meant to encompass a phenyl ring substituted with a hydroxyl group on any one of para-, ortho- or meta-positions of the ring relative to the point of attachment to the phenyl ring.

The expression "provided that when $R_5$ is hydrogen $R_6$ is substituted" is meant to encompass a fatty acid amide of general formula (I) wherein when the substituent $R_5$ is a hydrogen atom, $R_6$ is substituted by at least one group selected from —$C_1$-$C_6$ alkyl, —OH, —$OR_1$, —SH and —$SR_2$. In other embodiments, when $R_5$ is independently selected from —$C_1$-$C_6$ alkyl, —OH and —$OR_3$ (i.e. when $R_5$ is different from hydrogen), $R_6$ is optionally substituted by at least one group selected from —$C_1$-$C_6$ alkyl, —OH, —SH and —$SR_2$.

In some embodiments, $R_4$ is —OH.

In other embodiments, $R_5$ is —$C_1$-$C_6$ alkyl. In further embodiments, said —$C_1$-$C_6$ alkyl is methyl.

In other embodiments, $R_6$ is a —$C_{13}$-$C_{22}$ alkenyl. In further embodiments, said —$C_{13}$-$C_{22}$ alkenyl comprises between 1 to 6 double bonds.

The term "1 to 6 double bonds" is meant to encompass a —$C_{13}$-$C_{22}$ alkenyl chain having 1, 2, 3, 4, 5, or 6 double bonds. Each double bond may be in the cis or trans (or the E or Z) configuration and may be formed between any two carbon atoms on the alkenyl chain. In some embodiments, said —$C_{13}$-$C_{22}$ alkenyl comprises a single double bond.

In further embodiments, $R_6$ is substituted by at least one group selected from $C_1$-$C_6$ alkyl, —OH, —SH and —$SR_2$. In other embodiments, $R_6$ is substituted by at least two groups independently selected from —$C_1$-$C_6$ alkyl, —OH, —$OR_1$, —SH and —$SR_2$.

In further embodiments of the invention, $R_6$ is a substituent of formula (II):

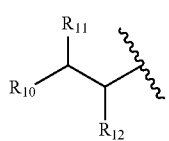

(II)

wherein $R_{10}$ is independently selected from —$C_{11}$-$C_{20}$ alkyl, —$C_{11}$-$C_{20}$ alkenyl and —$C_{11}$-$C_{20}$ alkynyl; and $R_{11}$ and $R_{12}$ are each independently selected from H, —$C_1$-$C_6$ alkyl, —OH, —SH and —$SR_2$.

In some other embodiments, $R_{10}$ is a —$C_{11}$-$C_{20}$ alkenyl. In other embodiments, said —$C_{11}$-$C_{20}$ alkenyl comprises between 1 to 6 double bonds. In yet other embodiments, said —$C_{11}$-$C_{20}$ alkenyl comprises a single double bond.

In other embodiments, $R_{11}$ is hydrogen. In further embodiments, $R_{11}$ is —$C_1$-$C_6$ alkyl. In yet further embodiments, said —$C_1$-$C_6$ alkyl is methyl.

In further embodiments, $R_{12}$ is hydrogen. In other embodiments, $R_{12}$ is —$C_1$-$C_6$ alkyl. In further embodiments, said —$C_1$-$C_6$ alkyl is methyl.

In other embodiments of the present invention, a fatty acid amide, including a stereoisomer and a salt thereof, is a compound of general formula (III):

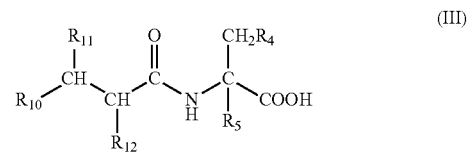

(III)

wherein $R_4$ is independently selected from —OH, —SH, phenyl and hydroxyl phenyl; $R_5$ is independently selected from H, —$C_1$-$C_6$ alkyl, —OH and —$OR_3$; $R_{10}$ is independently selected from —$C_1$-$C_{20}$ alkyl, —$C_{11}$-$C_{20}$ alkenyl and —$C_{11}$-$C_{20}$ alkynyl; $R_{11}$ and $R_{12}$ each are independently selected from H, —$C_1$-$C_6$ alkyl, —OH, —$OR_1$, —SH and —$SR_2$; wherein each of $R_1$, $R_2$, and $R_3$ is independently —$C_1$-$C_6$ alkyl; and provided that at least one of $R_5$, $R_{11}$ and $R_{12}$ is different from hydrogen.

The expression "provided that at least one of $R_5$, $R_{11}$ and $R_{12}$ is different from hydrogen" refers to a compound of general formula (III) wherein at least one of the substituents $R_5$, $R_{11}$ and $R_{12}$ is not a hydrogen atom. In some embodiments, when $R_5$ is hydrogen, at least one of $R_{11}$ and $R_{12}$ is individually selected from —$C_1$-$C_6$ alkyl, —OH, —SH and —$SR_2$. In other embodiments, when $R_{11}$ is hydrogen, $R_5$ is selected from —$C_1$-$C_6$ alkyl, —OH and —$OR_3$ and/or $R_{12}$ is selected from —$C_1$-$C_6$ alkyl, —OH, —$OR_1$, —SH and —$SR_2$. In further embodiments, when $R_{12}$ is hydrogen, $R_5$ is selected from —$C_1$-$C_6$ alkyl, —OH and —$OR_3$ and/or $R_{11}$ is selected from —$C_1$-$C_6$ alkyl, —OH, —$OR_1$, —SH and —$SR_2$.

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent, the substituents may be the same or different.

In some embodiments, a fatty acid amide of the invention is a compound of general formula (III), wherein $R_{10}$ is —$C_{11}$-$C_{20}$ alkenyl. In other embodiments, said —$C_{11}$-$C_{20}$ alkenyl comprises between 1 to 6 double bonds. In further embodiments, said —$C_{11}$-$C_{20}$ alkenyl comprises one double bond.

In other embodiments, a fatty acid amide of the invention is a compound of general formula (III), wherein $R_{10}$ is —$C_{11}$-$C_{20}$ alkenyl and $R_4$ is —OH.

In further embodiments, a fatty acid amide of the invention is a compound of general formula (III), wherein $R_{10}$ is —$C_{11}$-$C_{20}$ alkenyl, $R_4$ is —OH and $R_5$ is —$C_1$-$C_6$ alkyl. In some embodiments, said —$C_1$-$C_6$ alkyl is methyl.

In still other embodiments, a fatty acid amide of the invention is a compound of general formula (III), wherein $R_{10}$ is —$C_{11}$-$C_{20}$ alkenyl, $R_4$ is —OH, $R_5$ is —$C_1$-$C_6$ alkyl, $R_{11}$ is —$C_1$-$C_6$ alkyl and $R_{12}$ is H. In some embodiments, said —$C_1$-$C_6$ alkyl is methyl.

In yet additional embodiments, a fatty acid amide of the invention is a compound of general formula (III), wherein $R_{10}$ is $—C_{11}-C_{20}$ alkenyl, $R_4$ is —OH, $R_5$ is H, $R_{11}$ is $—C_1-C_6$ alkyl and $R_{12}$ is H. In some embodiments, said $—C_1-C_6$ alkyl is methyl.

In other embodiments, a fatty acid amide of the invention is a compound of general formula (III), wherein $R_{10}$ is $—C_{11}-C_{20}$ alkenyl, $R_4$ is —OH, $R_5$ is $—C_1-C_6$ alkyl, $R_{11}$ is $—C_1-C_6$ alkyl and $R_{12}$ is $—C_1-C_6$ alkyl. In some embodiments, said $—C_1-C_6$ alkyl is methyl.

In other embodiments, a fatty acid amide of the invention is a compound of general formula (III), wherein $R_{10}$ is $—C_{11}-C_{20}$ alkenyl, $R_4$ is —OH, $R_5$ is H, $R_{11}$ is $—C_1-C_6$ alkyl and $R_{12}$ is $—C_1-C_6$ alkyl. In some embodiments, said $—C_1-C_6$ alkyl is methyl.

In further embodiments, a fatty acid amide of the invention is a compound of general formula (III), wherein $R_{10}$ is $—C_{11}-C_{20}$ alkenyl, $R_4$ is —OH, $R_5$ is $—C_1-C_6$ alkyl, $R_{11}$ is $—C_1-C_6$ alkyl and $R_{12}$ is $—C_1-C_6$ alkyl. In some embodiments, said $—C_1-C_6$ alkyl is methyl.

In still other embodiments, a fatty acid amide of the invention is a compound of general formula (III), wherein $R_{10}$ is $—C_{11}-C_{20}$ alkenyl, $R_4$ is —OH, $R_5$ is $—C_1-C_6$ alkyl, $R_{11}$ is H and $R_{12}$ is H. In some embodiments, said $—C_1-C_6$ alkyl is methyl.

In additional embodiments, a fatty acid amide of the invention is a compound of general formula (III), wherein $R_{10}$ is $—C_{11}-C_{20}$ alkenyl, $R_4$ is —OH, $R_5$ is $—C_1-C_6$ alkyl, $R_{11}$ is H and $R_{12}$ is $—C_1-C_6$ alkyl. In some embodiments, said $—C_1-C_6$ alkyl is methyl.

In other embodiments, a fatty acid amide of the invention is a compound of general formula (III), wherein $R_{10}$ is $—C_{11}-C_{20}$ alkenyl, $R_4$ is —OH, $R_5$ is H, $R_{11}$ is H and $R_{12}$ is $—C_1-C_6$ alkyl. In some embodiments, said $—C_1-C_6$ alkyl is methyl.

In some embodiments of the invention, a fatty acid amide is a compound having the structure (1):

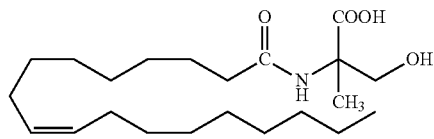

(1)

and any enantiomer or salt thereof.

In other embodiments of the invention, a fatty acid amide is a compound having the structure (2):

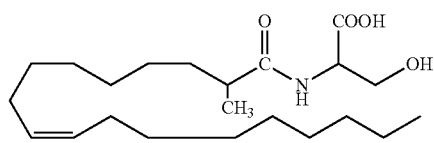

(2)

and any stereoisomer or salt thereof.

In yet further embodiments of the invention, a fatty acid amide is a compound having the structure (3):

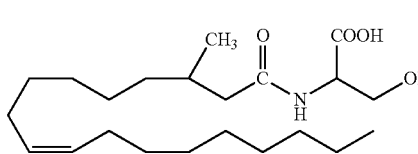

(3)

and any stereoisomer or salt thereof.

In another aspect, the invention encompasses a pharmaceutical composition comprising a fatty acid amide of the invention including any stereoisomer and salt thereof. The invention further provides a use of a fatty acid amide of the invention for the preparation of a pharmaceutical composition.

In some embodiments, the pharmaceutical composition of the invention is for stimulation of bone growth, bone mass, bone repair or prevention of bone loss.

The term "stimulation of bone growth, bone mass, bone repair" is meant to encompass any quantitative and/or qualitative promotion of growth of the osseous tissue, any quantitative and/or qualitative promotion of mass of the osseous tissue and any quantitative and/or qualitative promotion of osseous tissue repair (for example in the case any part of the osseous tissue is damaged or fractured for example after impact or as a consequence of a disease, condition or any side effect of an external treatment) in vertebrates at any development stage (from embryonic stage to elderly). In some embodiments, the pharmaceutical composition is for increasing bone mass in a subject in need thereof. In other embodiments, the pharmaceutical composition is for promoting bone repair.

The term "prevention of bone loss" is meant to encompass any quantitative and/or qualitative deterrence of osseous tissue loss in vertebrates at any development stage (from embryonic development stage to elderly).

In further embodiments, the pharmaceutical composition of the invention is for increasing the number of osteoblasts. In yet other embodiments, the pharmaceutical composition of the invention is for decreasing the number of osteoclasts.

In another aspect, the invention provides a fatty acid amide of the invention for the preparation of a pharmaceutical composition for the treatment of a medical conditions benefiting from stimulating bone growth, gain of bone mass, prevention and rescue of bone loss and bone repair. Non-limiting examples of medical conditions benefiting from stimulating bone growth, gain of bone mass, prevention and rescue of bone loss and bone repair are osteopenia, osteoporosis, bone fracture or deficiency, primary or secondary hyperparathyroidism, osteoarthritis, periodontal disease or defect, an osteolytic bone loss disease, post-plastic surgery, post-orthopedic surgery, post oral surgery, post-orthopedic implantation, and post-dental implantation, primary and metastatic bone cancer, osteomyelitis, or any combinations thereof. In some embodiments, a medical condition benefiting from stimulating bone growth is osteopenia or osteoporosis.

In another aspect, the invention provides a fatty acid amide of the invention for use in the stimulation of bone growth, bone mass, bone repair or prevention of bone loss. In some embodiments, a fatty acid amide of the invention is for the treatment of at least one disease or a disorder as recited above. In additional embodiments, said disease or disorder is selected from osteopenia, osteoporosis, bone fracture or deficiency, primary or secondary hyperparathyroidism, osteoarthritis, periodontal disease or defect, an osteolytic bone loss disease, post-plastic surgery, post-orthopedic surgery, post oral surgery, post-orthopedic implantation, and post-dental implantation, primary and metastatic bone cancer, osteomyelitis, or any combinations thereof. In other embodiments, said at least one disease or disorder is selected from osteopenia and osteoporosis.

In yet a further aspect, the invention encompasses a method of stimulation of bone growth, bone mass, bone repair or prevention of bone loss, said method comprising administering to a subject in need thereof a therapeutically effective amount of at least one fatty acid amide of the invention, or a composition comprising thereof. In some embodiments said method is for the treatment of at least one disease or a disorder as recited above. In some embodiments, said disease or disorder is selected from osteopenia, osteoporosis, bone fracture or deficiency, primary or secondary hyperparathyroidism, osteoarthritis, periodontal disease or defect, an osteolytic bone loss disease, post-plastic surgery, post-orthopedic surgery, post oral surgery, post-orthopedic implantation, and post-dental implantation, primary and metastatic bone cancer, osteomyelitis, or any combinations thereof. In other embodiments, said at least one disease or disorder is selected from osteopenia and osteoporosis.

The present invention also relates to a pharmaceutical composition comprising a fatty acid amide of the invention in combination (e.g., admixture) with a pharmaceutically acceptable auxiliary, and optionally at least one additional therapeutic agent. The auxiliary must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy. Such methods include the step of bringing in association fatty acid amides of the invention or combinations thereof with any auxiliary agent. The auxiliary agent(s), as the accessory ingredient(s), is typically selected from those conventional in the art, such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, dragées or capsules, or as a powder or granules, or as a solution or suspension. The active ingredient may also be presented as a bolus or paste. The compositions may further be processed into a suppository or enema for rectal administration.

The invention further includes a pharmaceutical composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The exact dose and regimen of administration of the composition will necessarily be dependent upon the effect to be achieved and may vary with the particular formula, the route of administration, and the age and condition of the individual subject to whom the composition is to be administered.

By another aspect the invention provides a use of a fatty acid amide of an amino acid, comprising a fatty acid moiety and an amino acid moiety, including a stereoisomer and a salt thereof for the preparation of a pharmaceutical composition for stimulation of bone growth, bone mass, bone repair or prevention of bone loss. It should be understood that this aspect of the invention encompasses fatty acid amides having optionally substituted fatty acid moiety and optionally substituted amino acid moiety.

In some embodiments, said use is for the preparation of a pharmaceutical composition for the treatment of at least one disease or a disorder as recited above. In some embodiments, said disease or disorder is selected from osteopenia, osteoporosis, bone fracture or deficiency, primary or secondary hyperparathyroidism, osteoarthritis, periodontal disease or defect, an osteolytic bone loss disease, post-plastic surgery, post-orthopedic surgery, post oral surgery, post-orthopedic implantation, and post-dental implantation, primary and metastatic bone cancer, osteomyelitis, or any combinations thereof. In other embodiments, said at least one disease or disorder is selected from osteopenia and osteoporosis.

In some embodiments, a fatty acid moiety of a fatty acid amide is selected from saturated fatty acid, mono-unsaturated fatty acid and poly unsaturated fatty acid. In further embodiments of the invention, a fatty acid moiety is an oleoyl fatty acid moiety ($CH_3(CH_2)_7CH=CH(CH_2)_7C(=O)—$).

In other embodiments, a fatty acid moiety of a fatty acid amide is substituted by at least one group selected from $—C_1$-$C_6$ alkyl, $—OH$, $—OR_1$, $—SH$ and $—SR_2$, wherein $R_1$ and $R_2$ are each independently $—C_1$-$C_6$ alkyl. In other embodiments, said at least one substituent of a fatty acid moiety is a $—C_1$-$C_6$ alkyl. In yet further embodiments, said $—C_1$-$C_6$ alkyl is methyl. In other embodiments, said at least one substitution of a fatty acid moiety of a fatty acid amide is on at least one of α- or β-positions of said fatty acid moiety.

In yet further embodiments, a fatty acid amide of the invention is substituted at the α-position of the fatty acid moiety of said fatty acid amide. In other embodiments, a fatty acid amide of the invention is substituted at the β-position of the fatty acid moiety of said fatty acid amide. In further embodiments, a fatty acid amide of the invention is substituted at the α- and β-positions of the fatty acid moiety of said fatty acid amide.

In further embodiments, said amino acid moiety of a fatty acid amide is derived from an amino acid selected from serine, cysteine, tyrosine and phenylalanine. In other embodiments, said amino acid moiety of a fatty acid amide is derived from serine. In some other embodiments, said amino acid moiety of a fatty acid amide is substituted by a group selected from $—C_1$-$C_6$ alkyl, $—OH$, and $—OR_3$, wherein $R_3$ is $—C_1$-$C_6$ alkyl. In further embodiments, said amino acid is substituted by $—C_1$-$C_6$ alkyl. In yet further embodiments, said $—C_1$-$C_6$ alkyl is methyl. In other embodiments, said substitution of an amino acid moiety of a fatty acid amide is on the α-position of said amino acid moiety.

In other embodiments, a fatty acid amide for use in the preparation of a pharmaceutical composition for stimulation of bone growth, bone mass, bone repair or prevention of bone loss, is a compound having general formula (I), wherein $R_4$ is independently selected from $—OH$, $—SH$, phenyl and hydroxyl phenyl; $R_5$ is independently selected from H, $—C_1$-$C_6$ alkyl, $—OH$ and $—OR_3$; $R_6$ is independently selected from $—C_{13}$-$C_{22}$ alkyl, $—C_{13}$-$C_{22}$ alkenyl and $—C_{13}$-$C_{22}$ alkynyl; optionally substituted by at least one group selected from —$C_1$-$C_6$ alkyl, —OH, —$OR_1$, —SH and —$SR_2$; wherein each of $R_1$, $R_2$, and $R_3$ is independently —$C_1$-$C_6$ alkyl; including a stereoisomer and a salt thereof.

In other embodiments, $R_4$ is —OH.

In further embodiments, $R_5$ is —$C_1$-$C_6$ alkyl. In further embodiments, said —$C_1$-$C_6$ alkyl is methyl.

In further embodiments, $R_6$ is a —$C_{13}$-$C_{22}$ alkenyl. In other embodiments, said —$C_{13}$-$C_{22}$ alkenyl comprises between 1 to 6 double bonds. In further embodiments, —$C_{13}$-$C_{22}$ alkenyl comprises one double bond. In other embodiments, $R_6$ is substituted by at least one group selected from —$C_1$-$C_6$ alkyl, —OH, —$OR_1$, —SH and —$SR_2$. In further embodiments, $R_6$ is substituted by at least two groups independently selected from —$C_1$-$C_6$ alkyl, —OH, —SH and —$SR_2$. In other embodiments, $R_6$ is a substituent of formula (II), wherein $R_{10}$ is independently selected from —$C_{11}$-$C_{20}$ alkyl, —$C_{11}$-$C_{20}$ alkenyl and —$C_{11}$-$C_{20}$ alkynyl; $R_{11}$ and $R_{12}$ are each independently selected from H, —$C_1$-$C_6$ alkyl, —OH, —$OR_1$, —SH and —$SR_2$.

In other embodiments, $R_{10}$ is a —$C_{11}$-$C_{20}$ alkenyl. In further embodiments, said —$C_{11}$-$C_{20}$ alkenyl comprises between 1 to 6 double bonds. In yet further embodiments, said —$C_{11}$-$C_{20}$ alkenyl comprises one double bond.

In other embodiments, $R_{11}$ is hydrogen. In further embodiments, $R_{11}$ is —$C_1$-$C_6$ alkyl. In yet further embodiments, said —$C_1$-$C_6$ alkyl is methyl.

In further embodiments, $R_{12}$ is hydrogen. In some other embodiments, $R_{12}$ is —$C_1$-$C_6$ alkyl. In yet other embodiments, said —$C_1$-$C_6$ alkyl is methyl.

In some other embodiments of the invention, a fatty acid amide for use in the preparation of a pharmaceutical composition for stimulation of bone growth, bone mass, bone repair or prevention of bone loss, is a compound having the general formula (III), including a stereoisomer and a salt thereof, wherein $R_4$ is independently selected from —OH, —SH, phenyl and hydroxyl phenyl; $R_5$ is independently selected from H, —$C_1$-$C_6$ alkyl, —OH and —$OR_3$; $R_{10}$ is independently selected from —$C_{11}$-$C_{20}$ alkyl, —$C_{11}$-$C_{20}$ alkenyl and —$C_{11}$-$C_{20}$ alkynyl; $R_{11}$ and $R_{12}$ are independently selected from H, —$C_1$-$C_6$ alkyl, —OH, —$OR_1$, —SH and —$SR_2$; wherein each of $R_1$, $R_2$, and $R_3$ is independently —$C_1$-$C_6$ alkyl.

In some embodiments, a fatty acid amide for use according to the invention is a compound of general formula (III), wherein $R_{10}$ is —$C_{11}$-$C_{20}$ alkenyl. In other embodiments, said —$C_{11}$-$C_{20}$ alkenyl comprises between 1 to 6 double bonds. In further embodiments, said —$C_{11}$-$C_{20}$ alkenyl comprises one double bond.

In other embodiments, a fatty acid amide for use according to the invention is a compound of general formula (III), wherein $R_{10}$ is —$C_{11}$-$C_{20}$ alkenyl and $R_4$ is —OH.

In other embodiments, a fatty acid amide for use according to the invention is a compound of general formula (III), wherein $R_{10}$ is —$C_{11}$-$C_{20}$ alkenyl, $R_4$ is —OH and $R_5$ is —$C_1$-$C_6$ alkyl. In some embodiments, said —$C_1$-$C_6$ alkyl is methyl.

In other embodiments, a fatty acid amide for use according to the invention is a compound of general formula (III), wherein $R_{10}$ is —$C_{11}$-$C_{20}$ alkenyl, $R_4$ is —OH, $R_5$ is —$C_1$-$C_6$ alkyl, $R_{11}$ is —$C_1$-$C_6$ alkyl and $R_{12}$ is H. In some embodiments, said —$C_1$-$C_6$ alkyl is methyl.

In other embodiments, a fatty acid amide for use according to the invention is a compound of general formula (III), wherein $R_{10}$ is —$C_{11}$-$C_{20}$ alkenyl, $R_4$ is —OH, $R_5$ is H, $R_{11}$ is —$C_1$-$C_6$ alkyl and $R_{12}$ is H. In some embodiments, said —$C_1$-$C_6$ alkyl is methyl.

In other embodiments, a fatty acid amide for use according to the invention is a compound of general formula (III), wherein $R_{10}$ is —$C_{11}$-$C_{20}$ alkenyl, $R_4$ is —OH, $R_5$ is —$C_1$-$C_6$ alkyl, $R_{11}$ is —$C_1$-$C_6$ alkyl and $R_{12}$ is —$C_1$-$C_6$ alkyl. In some embodiments, said —$C_1$-$C_6$ alkyl is methyl.

In other embodiments, a fatty acid amide for use according to the invention is a compound of general formula (III), wherein $R_{10}$ is —$C_{11}$-$C_{20}$ alkenyl, $R_4$ is —OH, $R_5$ is H, $R_{11}$ is —$C_1$-$C_6$ alkyl and $R_{12}$ is —$C_1$-$C_6$ alkyl. In some embodiments, said —$C_1$-$C_6$ alkyl is methyl.

In other embodiments, a fatty acid amide for use according to the invention is a compound of general formula (III), wherein $R_{10}$ is —$C_{11}$-$C_{20}$ alkenyl, $R_4$ is —OH, $R_5$ is —$C_1$-$C_6$ alkyl, $R_{11}$ is —$C_1$-$C_6$ alkyl and $R_{12}$ is —$C_1$-$C_6$ alkyl. In some embodiments, said —$C_1$-$C_6$ alkyl is methyl.

In other embodiments, a fatty acid amide for use according to the invention is a compound of general formula (III), wherein $R_{10}$ is —$C_{11}$-$C_{20}$ alkenyl, $R_4$ is —OH, $R_5$ is —$C_1$-$C_6$ alkyl, $R_{11}$ is H and $R_{12}$ is H. In some embodiments, said —$C_1$-$C_6$ alkyl is methyl.

In other embodiments, a fatty acid amide for use according to the invention is a compound of general formula (III), wherein $R_{10}$ is —$C_{11}$-$C_{20}$ alkenyl, $R_4$ is —OH, $R_5$ is —$C_1$-$C_6$ alkyl, $R_{11}$ is H and $R_{12}$ is —$C_1$-$C_6$ alkyl. In some embodiments, said —$C_1$-$C_6$ alkyl is methyl.

In other embodiments, a fatty acid amide for use according to the invention is a compound of general formula (III), wherein $R_{10}$ is —$C_{11}$-$C_{20}$ alkenyl, $R_4$ is —OH, $R_5$ is H, $R_{11}$ is H and $R_{12}$ is —$C_1$-$C_6$ alkyl. In some embodiments, said —$C_1$-$C_6$ alkyl is methyl.

In some other embodiments of the invention, a fatty acid amide for use as defined herein above is a compound having the formula (1), and any enantiomer and salt thereof.

In other embodiments of the invention, a fatty acid amide for use as defined herein above is a compound having the formula (2), and any stereoisomer and salt thereof.

In yet further embodiments of the invention, a fatty acid amide for use as defined herein above is a compound having the formula (3), or any stereoisomer and salt thereof.

The invention further provides a method of stimulation of bone growth, bone mass, bone repair or prevention of bone loss, said method comprising administering to a subject in need thereof a therapeutically effective amount of at least one fatty acid amide of an amino acid comprising a fatty acid moiety and an amino acid moiety, including a stereoisomer and a salt thereof. In some embodiments said method is for the treatment of at least one disease or a disorder as recited above. In some embodiments, said disease or disorder is selected from osteopenia, osteoporosis, bone fracture or deficiency, primary or secondary hyperparathyroidism, osteoarthritis, periodontal disease or defect, an osteolytic bone loss disease, post-plastic surgery, post-orthopedic surgery, post oral surgery, post-orthopedic implantation, and post-dental implantation, primary and metastatic bone cancer, osteomyelitis, or any combinations thereof. In other embodiments, said at least one disease or disorder is selected from osteopenia and osteoporosis.

In another aspect the invention provides a method of stimulation of bone growth, bone mass, bone repair or prevention of bone loss, said method comprising administering to a subject in need thereof a therapeutically effective amount of at least one compound of general formula (I), wherein $R_4$ is independently selected from —OH, —SH, phenyl and hydroxyl phenyl; $R_5$ is independently selected from H, —$C_1$-$C_6$ alkyl, —OH and —$OR_3$; $R_6$ is independently selected from —$C_{13}$-$C_{22}$ alkyl, —$C_{13}$-$C_{22}$ alkenyl and —$C_{13}$-$C_{22}$ alkynyl; optionally substituted by at least one group selected from —$C_1$-$C_6$ alkyl, —OH, —$OR_1$, —SH and —$SR_2$; wherein each of $R_1$, $R_2$, and $R_3$ is independently —$C_1$-$C_6$ alkyl; including a stereoisomer and a salt thereof. In some embodiments, said method is for the treatment of at least one disease or a disorder as recited above. In some embodiments, said disease or disorder is selected from osteopenia, osteoporosis, bone fracture or deficiency, primary or secondary hyperparathyroidism, osteoarthritis, periodontal disease or defect, an osteolytic bone loss disease, post-plastic surgery, post-orthopedic surgery, post oral surgery, post-orthopedic implantation, and post-dental implantation, primary and metastatic bone cancer, osteomyelitis, or any combinations thereof. In other embodiments, said at least one disease or disorder is selected from osteopenia and osteoporosis.

In another aspect, the invention encompasses a method of stimulating bone growth, bone mass, bone repair or prevention of bone loss, said method comprising administering to a subject in need thereof a therapeutically effective amount of at least one compound of general formula (III), wherein $R_4$ is independently selected from —OH, —SH, phenyl and hydroxyl phenyl; $R_5$ is independently selected from H, —$C_1$-$C_6$ alkyl, —OH and —$OR_3$; $R_{10}$ is independently selected from —$C_{11}$-$C_{20}$ alkyl, —$C_{11}$-$C_{20}$ alkenyl and —$C_{11}$-$C_{20}$ alkynyl; $R_{11}$ and $R_{12}$ are independently selected from H, —$C_1$-$C_6$ alkyl, —OH, —$OR_1$, —SH and —$SR_2$; wherein each of $R_1$, $R_2$, and $R_3$ is independently —$C_1$-$C_6$ alkyl; including a stereoisomer and a salt thereof.

In some embodiments, said method is for the treatment of at least one disease or a disorder as recited above. In some embodiments, said disease or disorder is selected from osteopenia, osteoporosis, bone fracture or deficiency, primary or secondary hyperparathyroidism, osteoarthritis, periodontal disease or defect, an osteolytic bone loss disease, post-plastic surgery, post-orthopedic surgery, post oral surgery, post-orthopedic implantation, and post-dental implantation, primary and metastatic bone cancer, osteomyelitis, or any combinations thereof. In other embodiments, said at least one disease or disorder is selected from osteopenia and osteoporosis.

The invention further provides a kit comprising at least one compound of the invention or a pharmaceutical composition comprising thereof, as hereinbefore described, and instructions for use thereof.

While anandamide (arachidonoyl ethanolamide), arachidonoyl serine (ARA-S; HU-362) and palmitoyl ethanolamide exhibited some osteoblastic proliferation activity, it was found that oleoyl serine was considerably more potent (FIG. 1).

Without being bound by theory as oleoyl serine may be hydrolyzed in vivo by amidases, oleoyl serine derivatives in which the amide bond is made more sterically hindered (for example by an introduction of a methyl group in close positions to the amide bond) and thus more difficult to approach by such enzymes, are considerably more potent than oleoyl serine itself. Examples of derivatives of oleoyl serine include oleoyl-α-methyl-serine (HU-671) and 2-methyl-oleoyl serine (HU-681). FIG. 2 presents non-limiting examples of fatty acid amides of the invention and related compounds.

FIG. 3 presents exemplary synthetic route for the synthetic manufacture of fatty acid amides of the invention.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 1(A)-1(F) are graphical depictions of screening of fatty acid derivatives identified in brain for proliferative activity in MC3T3 E1 osteoblastic cells. (A), oleoyl-serine (HU-639); (B), palmitoyl-serine; (C), arachidonoyl-serine (HU-362); (D), arachidonoyl-ethanolamide; (E), palmitoyl-ethanolamide; (F), 2-arachidonoylglycerol. Data are mean±SE obtained in 3 culture wells per condition.

FIGS. 5(A)-5(F) represents inhibition of osteoclast survival in ex vivo culture of mouse bone marrow-derived monocytes incubated for 4 days with M-CSF and RANKL. (A), number of intact osteoclasts with the use of oleoyl-serine (HU-639); (B), number of apoptotic osteoclasts; (C), representative photomicrograph of culture oleoyl-serine (HU-639)-free control culture; (D), representative photomicrograph of culture treated with $10^{-10}$ M oleoyl-serine (HU-639); (E), immunoblot analysis of Erk1/2 phosphorylation in preosteoclast-like RAW 264.7 cells. (F), RT-PCR analysis of RANKL and OPG expression in bone marrow-derived primary stromal cells. Quantitative data are mean±SE obtained in 3 culture wells per condition. Arrows indicate, apoptotic osteoclasts; *, ANOVA, $p<0.05$ vs. oleoyl-serine (HU-639)-free control (Cntl).

DETAILED DESCRIPTION OF EMBODIMENTS

Example 1

Synthesis of Acyl-Serines and Methylated Derivatives

Figure 2:
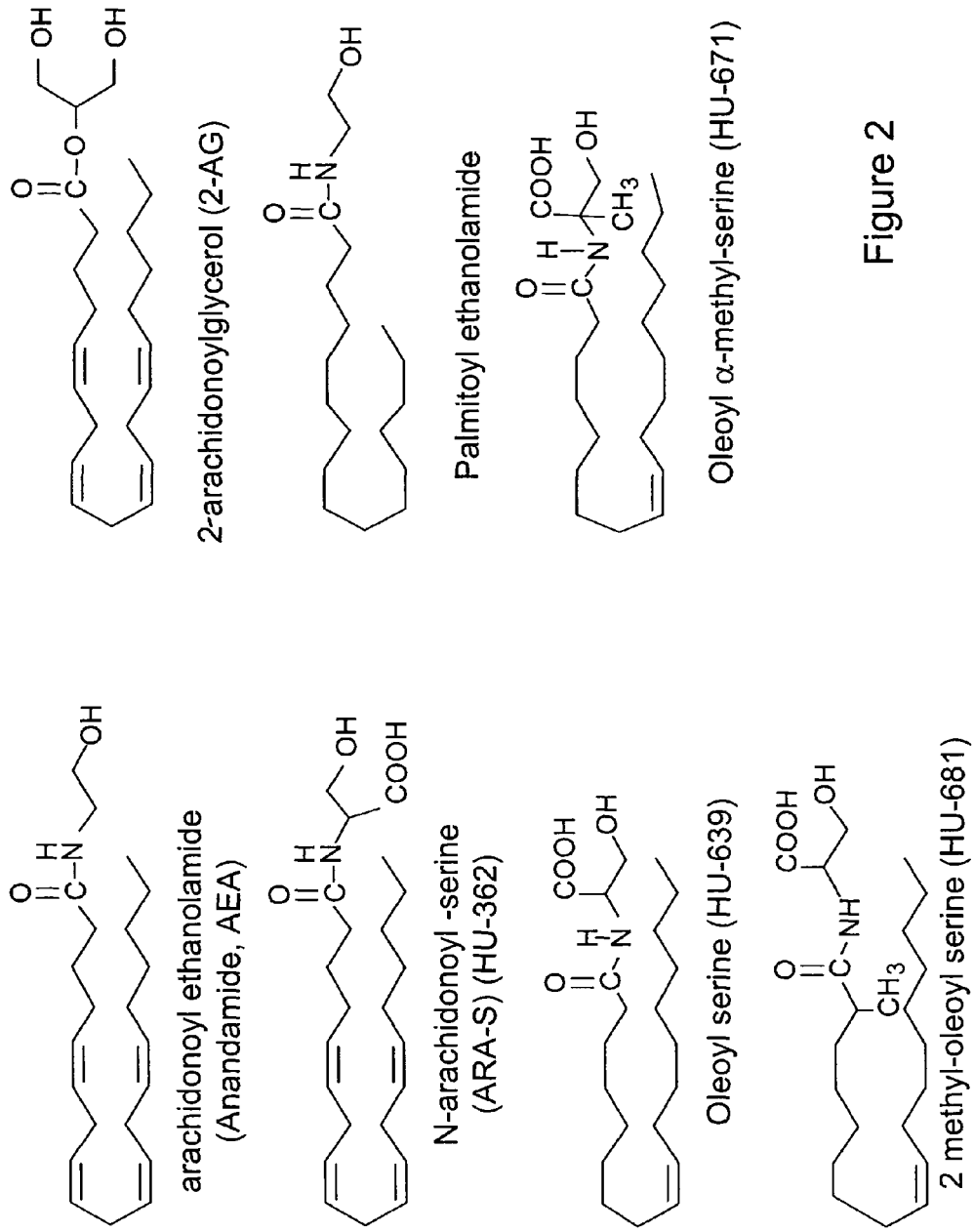
FIG. 2 shows schematic structures of compounds of the invention.
Figure 3A:
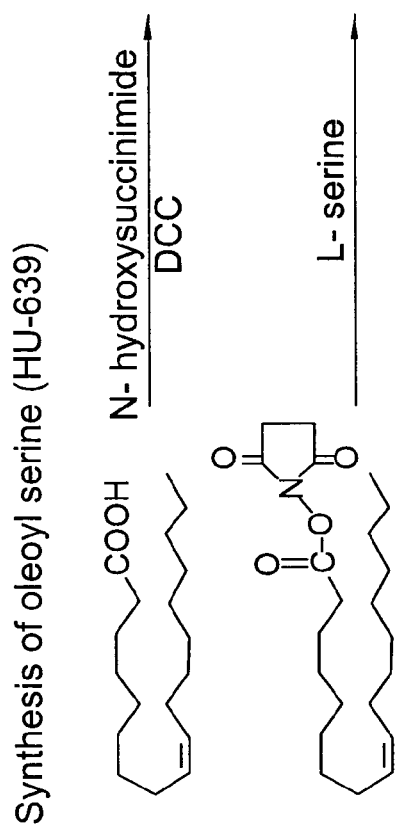
FIGS. 3(A)-3(C) shows a scheme of an exemplary synthesis of oleoyl serine (A), α-methyl oleoyl serine (B) and an exemplary synthesis of 2-methyl oleoyl serine (C).
Figure 3A:
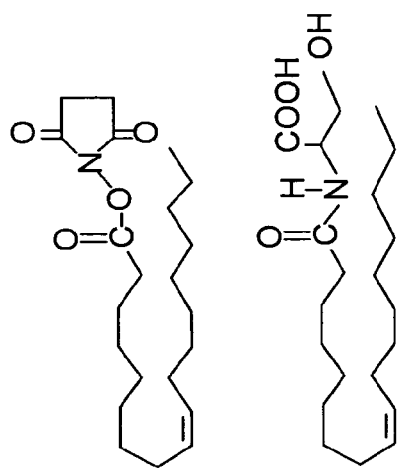
Figure 3B:
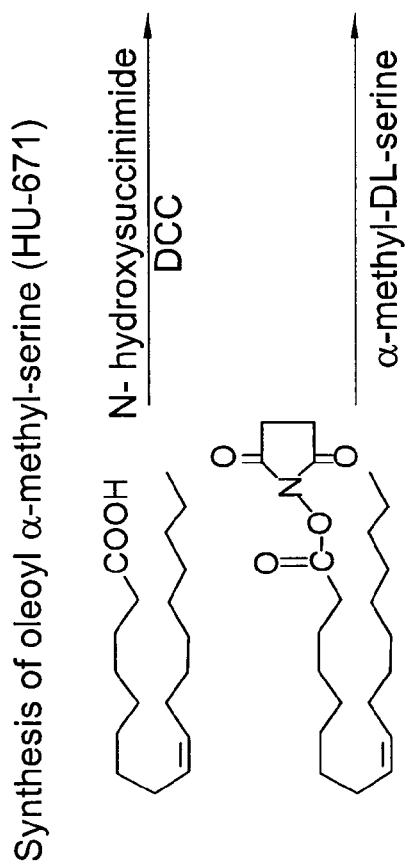
Figure 3B:
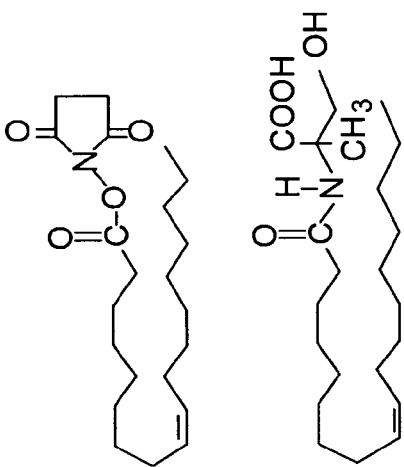
Figure 3C:
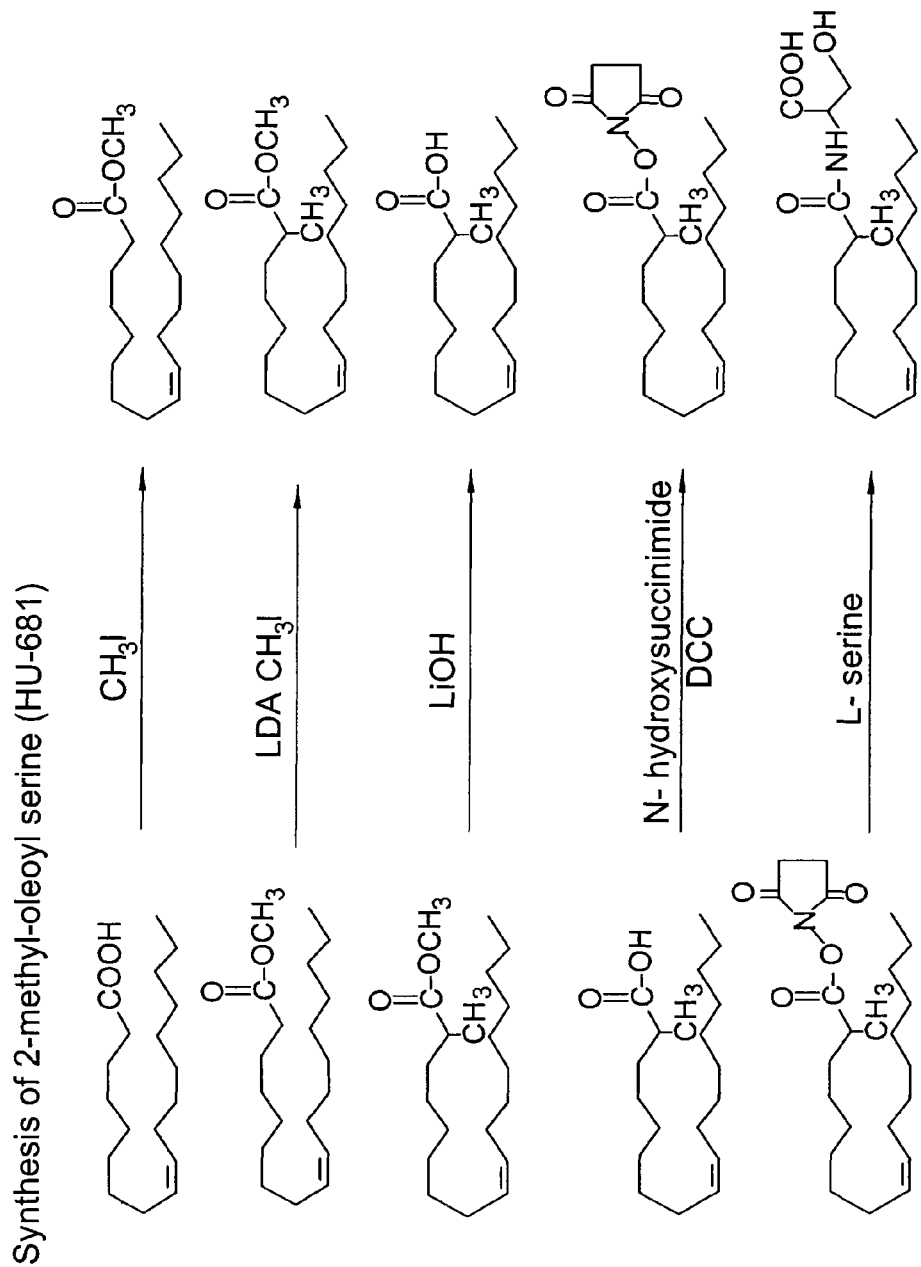

Synthesis of Oleoyl Serine
N-Hydroxysuccinimide Ester of Oleic Acid. Oleic acid (2 g, 7.08 mmoles) was added to a solution of N-hydroxysuccinimide (0.814 g, 7.08 mmoles) in dry ethyl acetate (30 ml). A solution of dicyclohexylcarbodiimide (1.45 g, 7.08 mmoles) in dry ethyl acetate (2.5 ml) was then added, and the reaction mixture was left overnight at room temperature Dicyclohexylurea was filtered, and the crude material was chromatographed on silica gel (eluting with chloroform) to give 2.38 g (85%) as yellowish oil.

N-Oleoyl L-Serine. A solution of hydroxysuccinimide ester of oleic acid (395 mg, 1 mmole) in tetrahydrofuran (10 ml) was added to a solution of L-serine (105 mg, 1 mmole) and sodium bicarbonate 84 mg, 1 mmole) in water (10 ml). The reaction mixture was let stirring overnight at room temperature, evaporated down to 10 ml, and acidified to pH 1 with 1 N HCl. The product was extracted with methylene chloride (2×20 mL) and dried (MgSO$_4$) and the solvent evaporated under reduced pressure. The crude material was chromatographed on silica gel (eluting with chloroform:methanol) to give 221.7 mg (60%) as a white powder, m.p. 118 C, NMR (CD$_3$OH, ppm): 5.35-5.32 (m, 2H), 4.57-4.36 (m, 1H), 3.90-3.85 (dd, J=12 Hz, 6 Hz, 1H), 3.82-3.78 (dd, J=12H$_z$, 6 H$_z$, 1H), 2.29-2.24 (t, 2H), 2.03-1.98 m, 4H), 1.68-1.58 (m, 2H), 1.32-1.29 (m, 22H), 0.91-0.87 (t, 3H). GC-MS (dTMS): 513, 498, 250, 132 m/z; LC-MS(-p): (M-H)$^+$=368 m/z.

Synthesis of N-Oleoly α-Methyl-DL-Serine
N-oleoly α-methyl-DL-serine. A solution of N-hydroxysuccinimide ester of oleic acid (395 mg, 1 mmole) in tetrahydrofuran (10 ml) was added to a solution of α-methyl-DL-serine (119.1 mg, 1 mmole) and sodium bicarbonate (84 mg, 1 mmole) in water (10 ml). The reaction mixture was left stirring overnight at room temperature, evaporated down to 10 ml, and acidified to pH 1 with 1 N HCl. The product was extracted with methylene chloride (2×20 mL) and dried (MgSO$_4$), and the solvent evaporated under reduced pressure. The crude material was chromatographed on silica gel (eluting with chloroform:methanol) to give 191.5 mg (50%) as a white powder. $^1$H NMR (CDCl$_3$) δ 0.911 (t, 3H), 1.302 (d, 20H), 1.597-1.612 (m, 5H), 2.054 (m, 4H), 2.283 (t, 2H), 3.860 (dd, 1H), 4.11 (dd, 1H), 4.503 (t, 1H), 5.37 (m, 2H).

Synthesis of 2-Methyl Oleoyl Serine
Methyl Oleate. Methyl oleate was prepared from oleic acid (Aldrich) and a 50 fold excess of HPLC grade methanol. The oleic acid (7 g, 0.0247 mol) was added to a 1 K 2-neck flask, equipped with a thermometer and a reflux condenser. A nitrogen adapter was connected to the condenser and the reaction vessel was purged of air in vacuo, and then refilled with dry N$_2$. The methanol (50.25 ml, 1.235 mol) along with 10 drops of 18 M H$_2$SO$_4$ and the mixture refluxed for 36-48 hrs. The crude product was extracted with ether, washed with water and dried over MgSO$_4$ and filtered. The solvent was removed in vacuo. The crude material was chromatographed on silica gel (eluting with 3% ether: petroleum ether) to give 4.5762 g (62.4%) as a colorless oil. Methyl 2-Methyl Oleate. Methyl oleate (3 gm, 10.13 mmol) in 30 ml dry THF was added dropwise to 2 equivalents of LDA solution (10.13 ml, 20.27 mmol of a 2.0M LDA solution in THF/heptane/ethylhexane) in 6 ml dry THF at (−40)-(−50)° C. for 45 min. It is critical that the reaction mixture was kept low during anion formation to avoid cis-trans isomerization of the double bonds. A ten fold excess of the methyl iodide was then added (101.3 mmol, 6.29 ml) rapidly with vigorous stirring and the red mixture immediately turned yellow. The reaction mixture was stirred for 90 min., allowing the bath and the reaction mixture to warm to room temperature and then poured into water and extracted with ether. The ether layers were washed with brine, dried (MgSO$_4$) and the solvent evaporated under reduced pressure. The rude material was chromatographed on silica gel (eluting with 1% ether: petroleum ether) to give 2.0118 g (64.1%) as a yellowish oil.

2-Methyl Oleic acid. To methyl 2-methyl oleate (2 gm, 6.4 mmol) were added 10 equivalents of lithium hydroxide (1.542 gm, 64 mmol) in 82 ml 3:1 methanol: H$_2$O (61.5 ml CH$_3$OH: 20.5 ml H$_2$O). The reaction was heated to 60° C. and monitored by TLC. The reaction was stopped after 5 hrs, acidified by 1N HCl until it is acidic, then extracted with ether. The ether extracts were dried (MgSO$_4$) and the solvent evaporated under reduced pressure to give 1.07 g (56.3%) as colorless oil.

N-HydroxysuccinimideEster of 2-Methyl Oleic acid. 2-Methyl Oleic acid (535.3 mg, 1.808 mmoles) was added to a solution of IN-hydroxysuccinimide 231.26 mg, 2.01 mmoles) in dry ethyl acetate (12.56 ml). After 5 min. stirring, a solution of dicyclohexylcarbodiimide (414.35 mg, 2.009 mmoles) in dry ethyl acetate (2.5 ml) was then added, and the reaction mixture was left stirring overnight at room temperature under nitrogen atmosphere. Dicyclohexylurea was filtered, and the crude material was chromatographed on silica gel (eluting with chloroform) to give 629 mg (85.05%) as yellowish oil.

2-Methyl Oleoyl-L-Serine. A solution of L-serine (190 mg, 1.8 mmol) in 20 ml. of 0.1 N sodium carbonate and 0.1 N sodium bicarbonate was added to a solution of N-hydroxysuccinimide ester of 2-methyl oleic acid (204.5 mg, 0.5 mmole) in 20 ml tetrahydrofuran. The reaction mixture was stirred overnight at 35° C., evaporated down to 20 ml, and acidified to pH 1 with 1 N HCl. The product was extracted with methylene chloride (2×20 mL), dried (MgSO$_4$), and the solvent evaporated under reduced pressure. The crude material was chromatographed on silica gel (eluting with chloroform:methanol) to give 86 mg (45%) as a yellowish oil $^1$H NMR (CDCl$_3$) δ 0.912 (t, 3H), 1.129 (d, 3H), 1.288 (s, 20H), 1.611 (m, 2H), 2.018 (m, 4H), 2.323 (m. 1H), 3.787 (dd, 1H), 3.980 (dd, 1H), 4.503 (t, 1H), 5.353 (m, 2H).

Example 2

Skeletal Activity of Oleoyl Serine

Figure 4A:
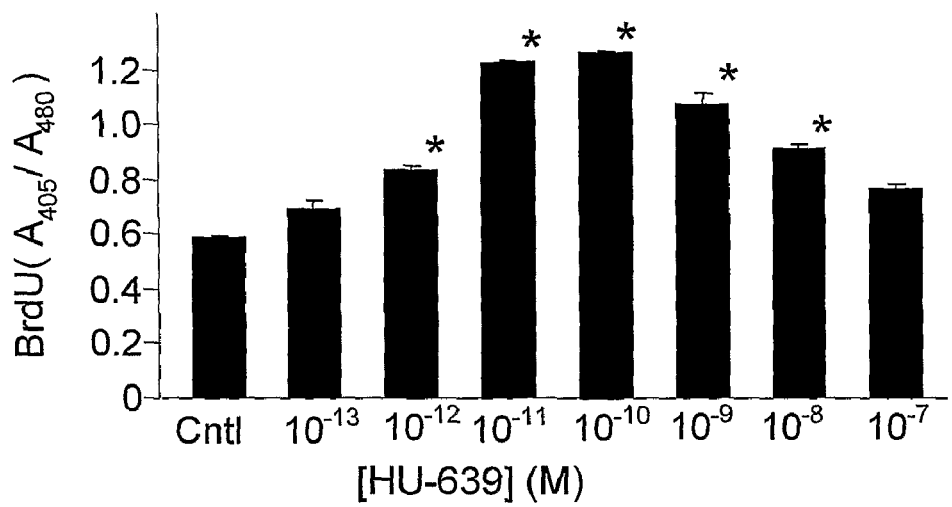
FIGS. 4(A)-4(E) represents signaling of oleoyl-serine (HU-639) in osteoblasts. *, ANOVA, $p<0.05$ vs. oleoyl-serine (HU-639)-free control (Cntl).
Figure 4B:
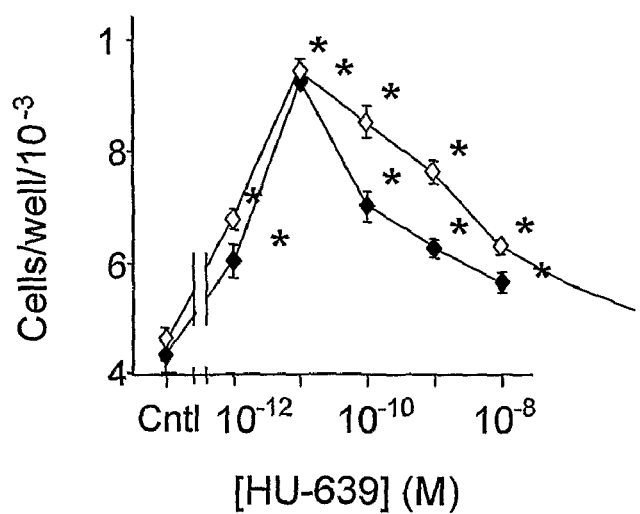
Figure 4C:
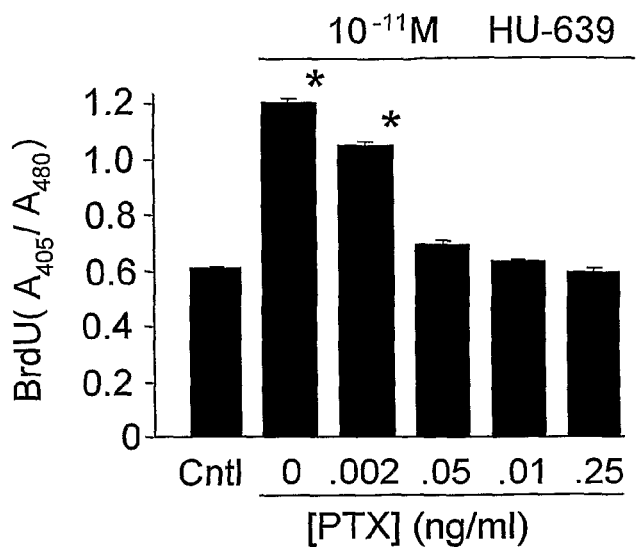
Figure 4D:
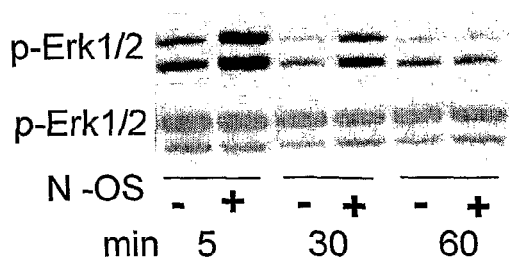
Figure 4E:
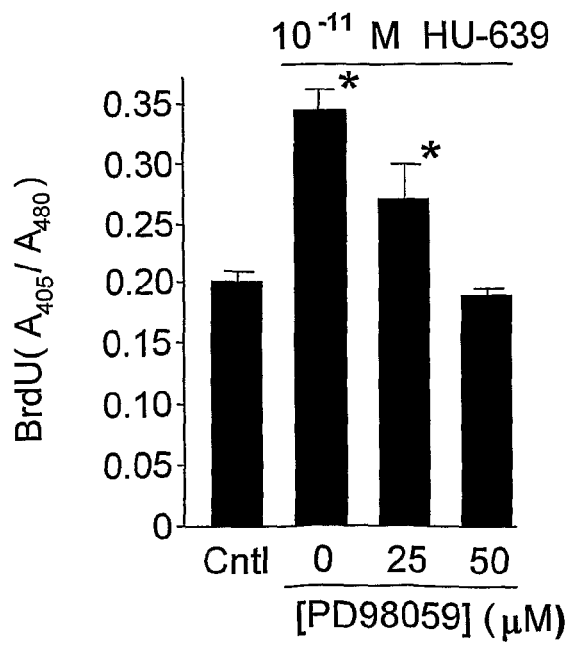

Several lipid compounds present in the brain stimulated the proliferation of MC3T3 E1 osteoblast-like cells in vitro (FIG. 1). Of these compounds, oleoyl-serine (HU-639) showed the highest potency, more than doubling cell number at $10^{-11}$ M concentration (FIG. 1). The HU-639 mitogenic effect was confirmed measuring BrdU incorporation in the MC3T3 E1 cells and in primary calvarial osteoblasts (FIG. 4A). Notably, calvarial osteoblasts derived from mice deficient of the CB2 cannabinoid receptor displayed a similar pattern of proliferative response to oleoyl-serine (HU-639) (FIG. 4B), suggesting that the oleoyl-serine (HU-639) effects are mediated by a receptor or receptors other than CB2. Typical of some osteoblast mitogenic agents [Miguel et al, 2005], the dose-response curves representing oleoyl-serine (HU-639) activity in culture are bell shaped, with the peak stimulation of cell number followed by reversal of the effect to baseline levels (FIGS. 4A, 4B). Nevertheless, like CB2, the putative main oleoyl-serine (HU-639) receptor is a Gi-protein coupled receptor inasmuch as the oleoyl-serine (HU-639) activity is inhabitable dose-dependently by pertusis toxin (FIG. 4C). Further downstream of the Gi-protein HU-639 stimulates Erk1/2 phosphorylation (FIG. 4D). Inhibition of Erk1/2 phosphorylation by the MEK inhibitor PD98059 blocks the oleoyl-serine (HU-639) mitogenic activity dose-dependently (FIG. 4E).

Figure 5A:
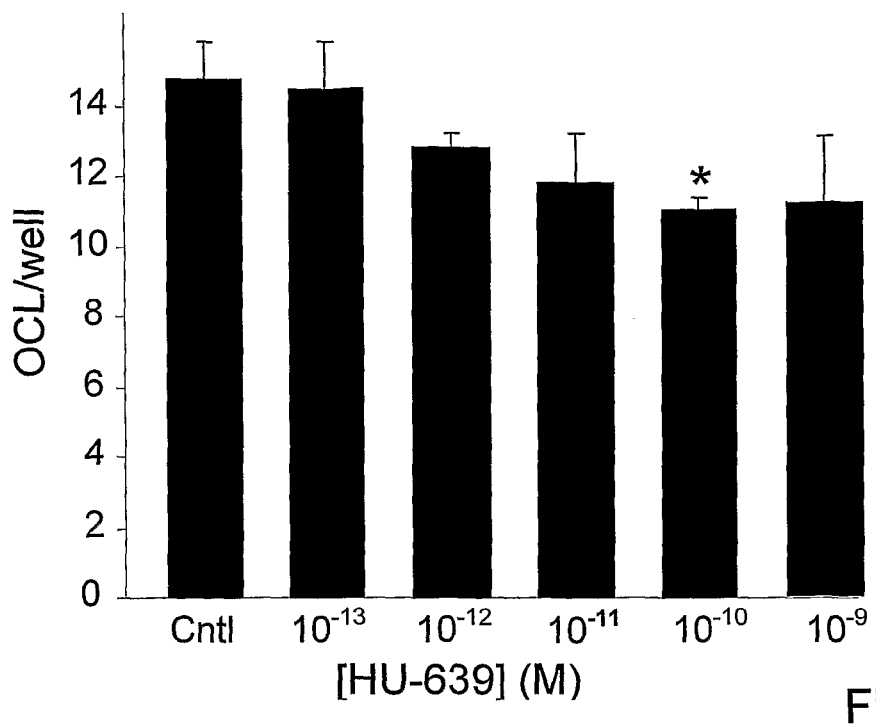
Figure 5B:
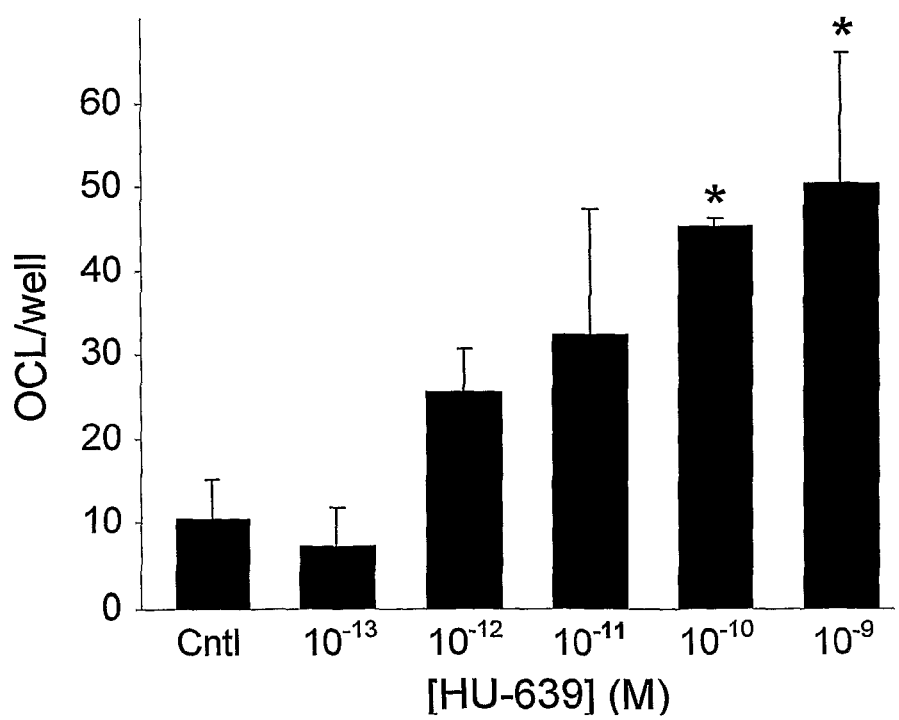

In addition to the stimulation of osteoblast number, oleoyl-serine (HU-639) inhibits osteoclast survival in ex vivo cultures of bone marrow-derived monocytes grown in the presence of RANKL and macrophage-colony stimulating factor (FIGS. 5A, 5C, 5D) by stimulating osteoclast apoptosis (FIGS. 5B, 5D). The reduced osteoclast survival is accompanied by reduced Erk phosphorylation, mainly p42 (FIG. 5E); it is only partially cell autonomous, as oleoyl-serine (HU-639) also inhibits RANKL expression in bone marrow stromal cells (FIG. 5F). This inhibition is likely to have a restraining effect on osteoclast survival [Kim et al, 2009].

Figure 6:
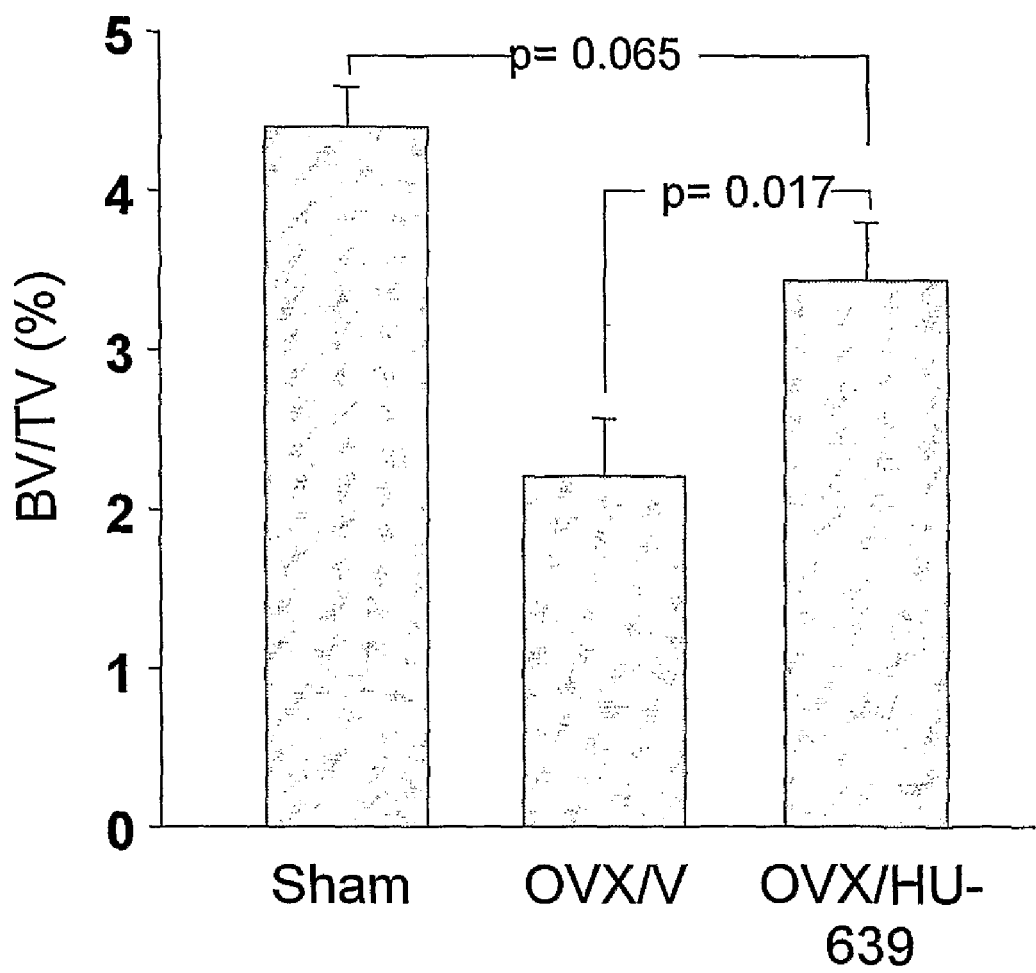
FIG. 6 oleoyl-serine (HU-639) rescues ovariectomy (OVX)-induced trabecular bone loss in mouse distal femoral metaphysis. Mice were OVXed or sham-OVXed and left untreated for 6 weeks to allow for bone loss. Thereafter, OVXed mice were treated by i.p. administration of oleoyl-serine (HU-639), 5 mg/Kg/day for 6 weeks and subjected to qualitative and quantitative analysis by microcomputed tomography. BV/TV, trabecular bone volume density. VEH, ethanol/emulphor/saline solvent. Data are mean±SE obtained in 6-8 mice per condition.
Figures 7A, 7B, 7C:
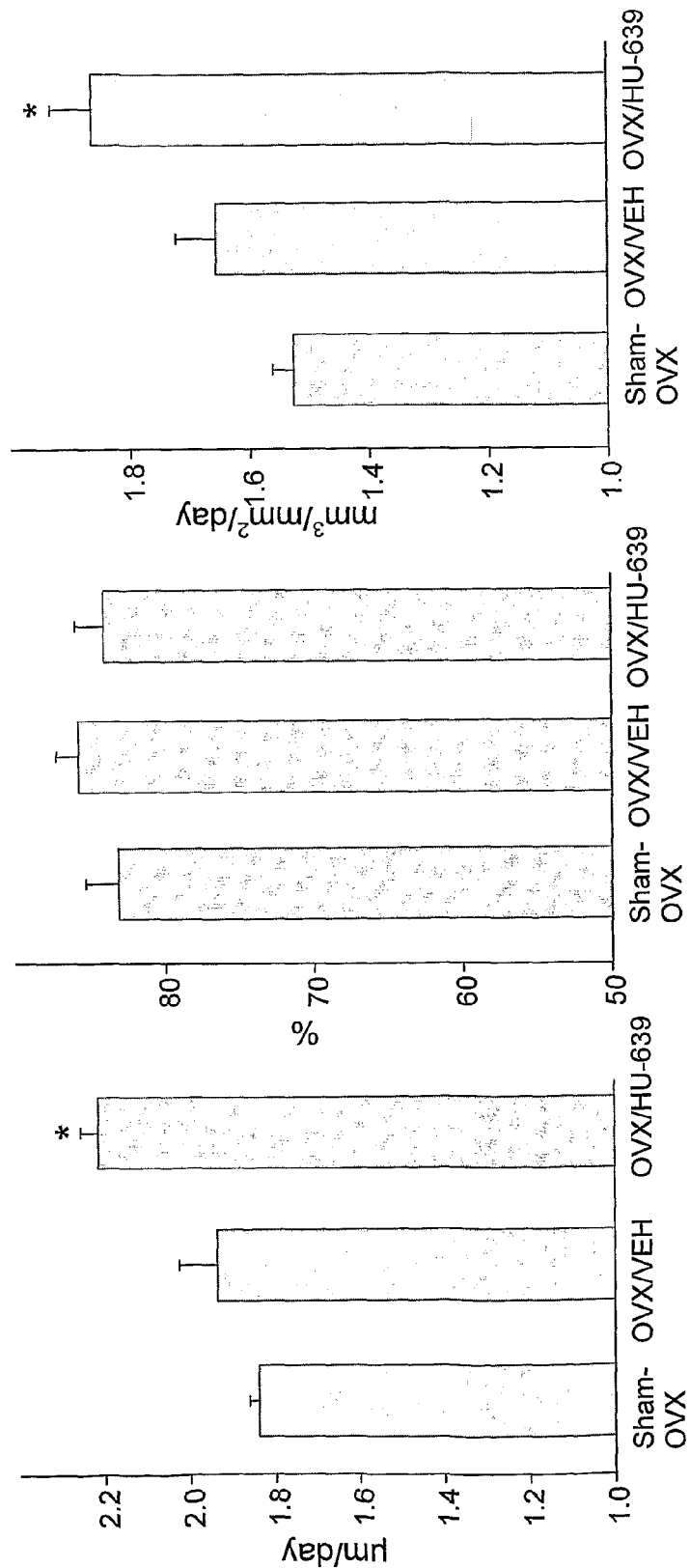
FIG. 7 represents stimulation of trabecular bone formation in distal femoral metaphysis of ovariectomized (OVX) mice using oleoyl-serine (HU-639). Same mice shown in FIG. 4. VEH, ethanol/emulphore/saline solvent. Histomorphometric analysis based on vital labeling of newly formed bone by calcein. Data are mean±SE obtained in 6-8 mice per condition. *, ANOVA, $p<0.05$ vs. Sham-OVX.
Figure 8:
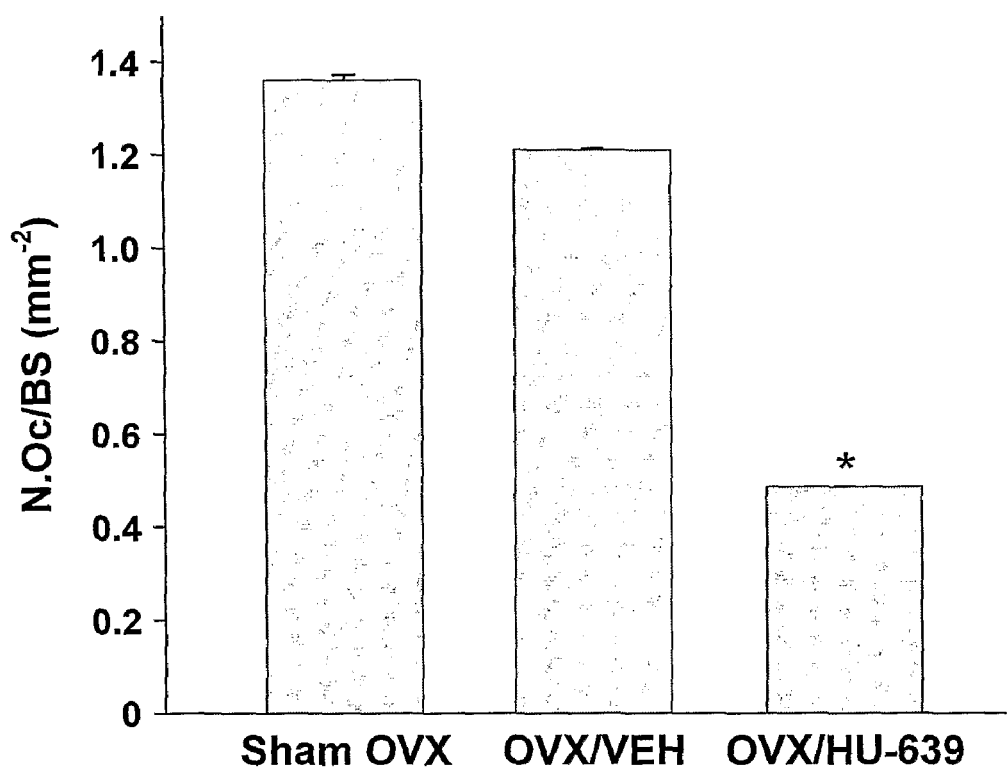
FIG. 8 represents decreasing of osteoclast number in distal femoral metaphysical trabecular bone in of ovariectomized (OVX) mice using oleoyl-serine (HU-639). Same mice shown in FIGS. 4 & 5. VEH, ethanol/emulphore/saline solvent. Osteoclast counts were based on osteoclast specific staining with tartrate-resistant acid phosphatase. Data are mean±SE obtained in 6-8 mice per condition. *, ANOVA, $p<0.05$ vs. Sham-OVX and OVX/VEH.

Based on the in vitro screening, the in vivo skeletal activity of oleoyl-serine (HU-639) in an ovariectomy (removal of ovaries; OVX) mouse model, the most widely used animal model for osteoporosis, was analyzed. Using this experimental system for testing bone anabolic activity, OVXed mice are left untreated to allow for bone loss to occur, followed by a treatment period intended for reversal of the bone loss [Alexander et al, 2001]. In the present study, a micro-computed tomographic (μCT) analysis indicated that in the distal femoral metaphysis, oleoyl-serine (HU-639) significantly reversed more than 50% of the OVX-induced trabecular bone loss within a six-week treatment period (FIG. 6). This effect is greater than the reversal of bone volumetric density by parathyroid hormone (1-34), the only clinically approved bone anabolic agent [Alexander et al, 2001]. The difference in trabecular bone volume density (BV/TV) between the oleoyl-serine (HU-639) treated mice and vehicle treated OVXed controls was statistically insignificant. To further elucidate the process leading to the oleoyl-serine (HU-639) rescue of OVX-induced bone loss, the same mice were subjected to an analysis of bone formation and resorption by computerized histomorphometry (HM). As expected, trabecular bone formation parameters in the vehicle treated animals did not differ from the sham OVXed controls, indicating that the OVX-induced bone loss has ceased and a new remodeling balance has been established. Typical of a bone anabolic agent, oleoyl-serine (HU-639) stimulated mineral appositional rate (MAR), leading to the stimulation of overall bone formation (FIG. 7). The OVX-induced enhancement of bone formation was statistically significant when compared to both sham- and vehicle-treated OVXed controls. As in culture, oleoyl-serine (HU-639) markedly inhibited bone resorption, represented by osteoclast counts based on tartrate resistant acid phosphatase (TRAP) staining (FIG. 8).

Example 3

Figure 9A:
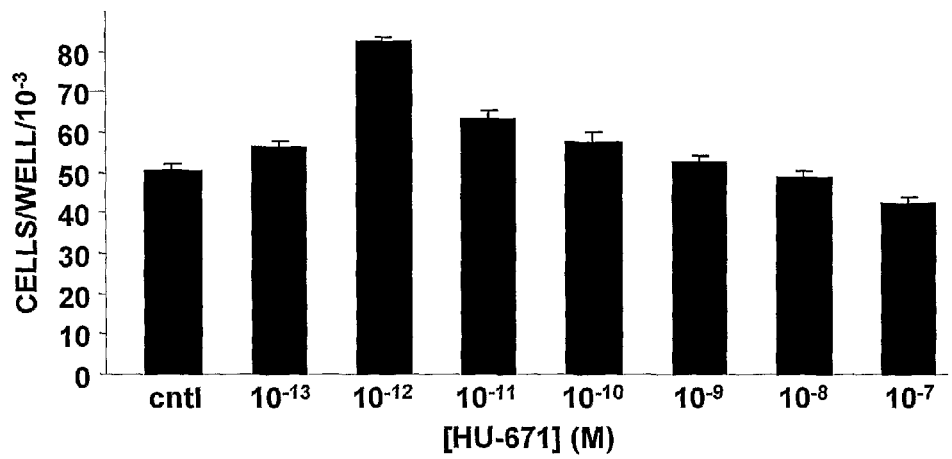
FIG. 9 represents methylated oleoyl-serine (HU-639) derivatives α-methyl oleoyl serine (HU-671) and 2-methyl-oleoyl serine (HU-681)) stimulation of MC3T3 E1 osteoblastic cell number at concentration 10- to 100-fold lower than HU-639. Data are mean±SE obtained in 3 culture wells per condition. *, ANOVA, p<0.05 vs. ligand-free control (Cntl).
Figure 9B:
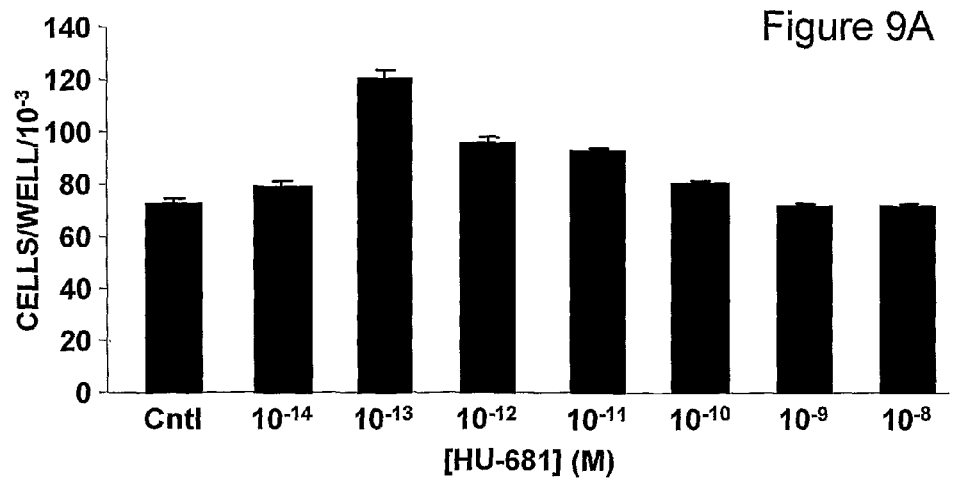

Enhanced Stimulation of Osteoblast Number by Methylated Derivatives of Oleoyl Serine The oleoyl-serine derivatives α-methyl oleoyl serine (HU-671) and 2-methyl-oleoyl serine (HU-681) were tested in the MC3T3 E1 osteoblastic cell assay, HU-671 and HU-681 stimulated cell number with respective peak effects at $10^{-12}$ M and $10^{-13}$ M as compared to $10^{-11}$ M of the parent HU-639 molecule (FIG. 9).

REFERENCES

Abe E, Marians R C, Yu W, Wu X B, Ando T, Li Y, Iqbal J. Eldeiry L, Rajendren G, Blair H C, Davies T F, Zaidi M (2003). TSH is a negative regulator of skeletal remodeling. *Cell*. 115: 151-162.

Alexander J M, Bab I, Fish S, Muller R, Uchiyama T, Gronowicz G, Nahounou M, Zhao Q, White D W, Chorev M, Gazit D, Rosenblatt M (2001) Human parathyroid hormone 1-34 reverses bone loss in ovariectomized mice. *J. Bone Miner Res.* 16:1665-1673.

Allison S J, Herzog H (2006) NPY and bone. *EXS*. 95: 171-182.

Bab, I. (2005) The skeleton: stone bones and stoned heads? In: Mehoulam R., Ed.: Cannabinoids as Therapeutics. Milestones in Drug Therapy Series, Birkhäuser Verlag, Basel, pp. 201-206.

Bab I A (2007) Regulation of Skeletal Remodeling by the Endocannabinoid System. *Annals of the New York Academy of Sciences*, Epub ahead of print.

Bab I, Zimmer A. (2008) Cannabinoid receptors and the regulation of bone mass. *Br J. Pharmacol*. 153: 182-188.

Devane W A, Hanus L, Breuer A, Pertwee R G, Stevenson L A, Griffin G, Gibson D, Mandelbaum A, Etinger A, Mechoulam R (1992) Isolation and structure of a brain constituent that binds to the cannabinoid receptor. *Science*. 258: 1946-1949.

Elefteriou F, Aim J D, Takeda S, Starbuck M, Yang X, Liu X, Kondo H, Richards W G, Bannon T W, Noda M, Clement K, Vaisse C, Karsenty G (2005) Leptin regulation of bone resorption by the sympathetic nervous system and CART. *Nature*. 434: 514-520.

Idris A I, van't H of R J, Greig I R, Ridge S A, Baker D, Ross R A, Ralston S H (2005) Regulation of bone mass, bone loss and osteoclast activity by cannabinoid receptors. *Nature Medicine* 11:774-779.

Karsak M, Cohen-Solal M, Freudenberg J, Ostertag A, Morieux C, Kornak U, Essig J. Erxlebe E, Bab I, Kubisch C, de Vernejoul M-C Zimmer A (2005) The cannabinoid receptor type 2 (CNR2) gene is associated with human osteoporosis. Human Molecular Genetics 14: 3389-3396.

Kim H, Choi H K, Shin J H, Kim K H, Huh J Y, Lee S A, Ko C Y, Kim H S, Shin H I, Lee H J, Jeong D, Kim N, Choi Y, Lee S Y. (2009) Selective inhibition of RANK blocks osteoclast maturation and function and prevents bone loss in mice. *J. Clin. Invest*. Epub ahead of Print.

Lin S, Boey D, Herzog H (2004) NPY and Y receptors: lessons from transgenic and knockout models. *Neuropeptides*. 38: 189-200.

Mechoulam R, Ben-Shabat S, Hanus L, Ligumsky M, Kaminski N E, Schatz A R, Gopher A, Almog S, Martin B R, Compton D R, et al. (1995) Identification of an endogenous 2-monoglyceride, present in canine gut, that binds to cannabinoid receptors. *Biochemical Pharmacology*. 50: 83-90.

Miguel S M, Namdar-Attar M, Noh T, Frenkel B, Bab I (2005) ERK1/2 activated de novo Mapkapk2 synthesis is essential for osteogenic growth peptide mitogenic signaling in osteoblastic cells. *Journal of Biological Chemistry*. 280: 37495-37502.

Milman G, Maor Y, Abu-Lafi S, Horowitz M, Gallily R, Batkai S, Mo F M, Offertaler L, Pacher P, Kunos G, Mechoulam R (2006) N-arahidonoyl L-serine, an endocannabinoid-like brain constituent with vasodilatory properties. *Proceedings of the National Academy of Sciences of the United States of America.* 103: 2428-2433.

Ofek O, Karsak M, Leclerc N, Fogel M, Frenkel B, Wright K, Tam J, Attar-Namdar M, Kram V, Shohami E, Mehoulam R, Zimmer A, Bab I (2006) Peripheral cannabinoid receptor, CB2, regulates bone mass. *Proceedings of the National Academy of the United States of America.* 103: 696-701.

Patel M S, Elefteriou F (2007) The new field of neuroskeletal biology. *Calcified Tissue International.* 80: 337-347.

Robling A G, Castillo A B, Turner C H (2006) Biomechanical and Molecular Regulation of Bone Remodeling. *Annual Review of Biomedical Engineering.* Epub ahead of print.

Rosen V (2006) BMP and BMP inhibitors in bone. *Annals of the New York Academy of Sciences.* 1068: 19-25.

Scutt A, Williamson E M (2007) Cannabinoids stimulate fibroblastic colony formation by bone marrow cells indirectly via CB2 receptors. *Calcified Tissue International.* 80: 50-59.

Sun L, Peng Y, Sharrow A C, Iqbal J. Zhang Z, Papachristou D J, Zaidi S, Zhu L L, Yaroslayskiy B B, Zhou H, Zallone A, Sairam M R, Kumar T R, Bo W, Braun J, Cardoso-Landa L, Shaffler M B, Moonga B S, Blair H C, Zaidi M (2006) FSH directly regulates bone mass. *Cell.* 125: 247-260.

Takeda S, Elefteriou F, Levasseur R, Liu X, Zhao L, Parker K L, Armstrong D, Ducy P, Karsenty G (2002) Leptin regulates bone formation via the sympathetic nervous sytem. *Cell.* 111: 305-317.

Tam J, Ofek O, Fride E, Ledent C, Gabet Y, Muller R, Zimmer A, Mackie K, Mechoulam R, Shohami E, Bab I (2006) Involvement of neuronal cannabinoid receptor CB1 in regulation of bone mass and bone remodeling. *Molecular Pharmacology.* 70: 786-792.

Tam J. Trembovler V, Di Marzo V, Petrosino S, Leo G, Alexandrovich A, Regev E Casap N, Shteyer A, Ledent C, Karsak M, Zimmer A, Mechoulam R, Yirmiya R, Shohami E, Bab I (2008) The Cannabinoid CB1 Receptor Regulates Bone Formation by Modulating Adrenergic Signaling, *Faseb Journal* 22:285-294.

The invention claimed is:

1. A method of stimulation of bone growth, bone mass, bone repair or prevention of bone loss, the method comprising:
    administering to a subject in need thereof a therapeutically effective amount of at least one fatty acid amide of an amino acid, including a stereoisomer and a salt thereof, wherein
        the fatty acid moiety is optionally substituted on at least one of the α- or β-positions of the fatty acid moiety by at least one group selected from the group consisting of —$C_1$-$C_6$ alkyl, —OH, —$OR_1$, —SH and —$SR_2$, and
        the amino acid moiety being selected from the group consisting of alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine,
        the amino acid moiety being optionally substituted at the α-position of the amino acid moiety by at least one group selected the group consisting of from —$C_1$-$C_6$ alkyl, —OH and —$OR_3$,
    $R_1$, $R_2$, $R_3$ are each independently —$C_1$-$C_6$ alkyl,
    provided that at least one of the fatty acid moiety and the amino acid moiety is substituted.

2. The method according to claim 1, wherein the fatty acid amide is a compound of general formula (I), including a stereoisomer and a salt thereof:

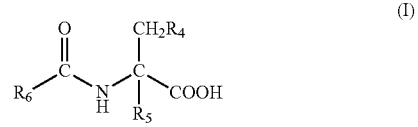

wherein
    $R_4$ is independently selected from the group consisting of —OH, —SH, phenyl and hydroxyl phenyl,
    $R_5$ is independently selected from the group consisting of H, —$C_1$-$C_6$ alkyl, —OH and —$OR_3$,
    $R_6$ is independently selected from the group consisting of —$C_{13}$-$C_{22}$ alkyl, —$C_{13}$-$C_{22}$ alkenyl and —$C_{13}$-$C_{22}$ alkynyl and is optionally substituted by at least one group selected from the group consisting of —$C_1$-$C_6$ alkyl, —OH, —$OR_1$, —SH and —$SR_2$,
    $R_1$, $R_2$, $R_3$ are each independently —$C_1$-$C_6$ alkyl,
    provided that when $R_5$ is hydrogen $R_6$ is substituted.

3. The method according to claim 2, wherein $R_6$ is a substituent of formula (II):

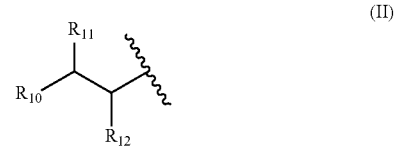

wherein
    $R_{10}$ is independently selected from the group consisting of —$C_{11}$-$C_{20}$ alkyl, —$C_{11}$-$C_{20}$ alkenyl and —$C_{11}$-$C_{20}$ alkynyl, and
    $R_{11}$ and $R_{12}$ are each independently selected from the group consisting of H, —$C_1$-$C_6$ alkyl, —OH, —$OR_1$, —SH and —$SR_2$.

4. The method according to claim 1, wherein the fatty acid amide is a compound of general formula (III), including a stereoisomer and a salt thereof:

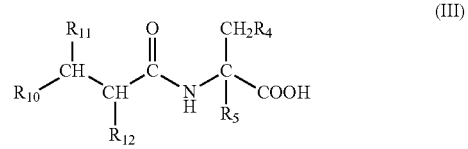

wherein
    $R_4$ is independently selected from the group consisting of —OH, —SH, phenyl and hydroxyl phenyl,
    $R_5$ is independently selected from the group consisting of H, —$C_1$-$C_6$ alkyl, —OH and —$OR_3$,
    $R_{10}$ is independently selected from the group consisting of —$C_{11}$-$C_{20}$ alkyl, —$C_{11}$-$C_{20}$ alkenyl and —$C_{11}$-$C_{20}$ alkynyl,
    $R_{11}$ and $R_{12}$ each are independently selected from the group consisting of H, $C_1$-$C_6$ alkyl, —OH, —$OR_1$, —SH and —$SR_2$,
    $R_1$, $R_2$, $R_3$ are each independently —$C_1$-$C_6$ alkyl, provided that at least one of $R_5$, $R_{11}$ and $R_{12}$ is different from hydrogen.

5. The method according to claim 1, where the fatty acid amide is a compound of general formula IV:

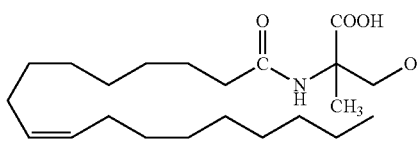

(IV)

and any enantiomer and salt thereof.

6. The method according to claim 1, wherein the fatty acid amide is a compound of general formula V:

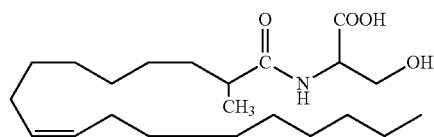

(V)

and any stereoisomer or salt thereof.

7. A pharmaceutical composition, comprising:
the fatty acid amide according to claim 1, or any stereoisomer or salt thereof.

8. The method according to claim 1, wherein the stimulation of bone growth, bone mass, bone repair or prevention of bone loss is associated with at least one disease or a disorder selected from the group consisting of osteopenia, osteoporosis, bone fracture or deficiency, primary hyperparathyroidism, secondary hyperparathyroidism, osteoarthritis, periodontal disease or defect, an osteolytic bone loss disease, post-plastic surgery, post-orthopedic surgery, post oral surgery, post-orthopedic implantation, post-dental implantation, primary bone cancer, metastatic bone cancer, and osteomyelitis, or any combinations thereof.

9. A fatty acid amide of an amino acid, being a compound of general formula (III), including a stereoisomer and a salt thereof:

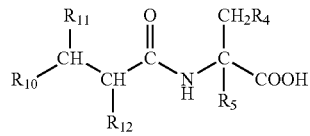

(III)

wherein
$R_4$ is —OH;
$R_5$ is selected from the group consisting of H, —$C_1$-$C_6$ alkyl, —OH and —$OR_3$;

$R_{10}$ is —$C_{11}$-$C_{20}$ alkenyl;
$R_{11}$ and $R_{12}$ each are independently selected from the group consisting of H, —$C_1$-$C_6$ alkyl, —$OR_1$, —SH and —$SR_2$;
$R_1$, $R_2$, $R_3$ are each independently —$C_1$-$C_6$ alkyl;
provided that at least one of $R_5$, $R_{11}$ and $R_{12}$ is different from hydrogen.

10. The fatty acid amide according to claim 9, wherein the fatty acid amide is a compound of general formula IV:

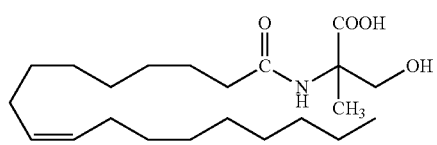

(IV)

and any enantiomer or salt thereof.

11. The fatty acid amide according to claim 9, wherein the fatty acid amide is a compound of general formula V

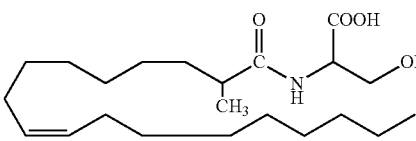

(V)

and any stereoisomer or salt thereof.

12. A pharmaceutical composition, comprising:
the fatty acid amide of claim 9 or any stereoisomer or salt thereof.

13. A method of treating a disease or disorder in a subject in need thereof, the method comprising:
administering to the subject an effective amount of the fatty acid amide according to claim 9, wherein the disease or disorder is selected from the group consisting of osteopenia, osteoporosis, bone fracture or deficiency, primary hyperparathyroidism, secondary hyperparathyroidism, osteoarthritis, periodontal disease or defect, an osteolytic bone loss disease, post-plastic surgery, post-orthopedic surgery, post oral surgery, post-orthopedic implantation, and post-dental implantation, primary bone cancer, awl metastatic bone cancer and osteomyelitis, or any combinations thereof.

14. A method for stimulation of bone growth, bone mass, bone repair or prevention of bone loss, the method comprising:
administering to a subject in need thereof a therapeutically effective amount of the at least one fatty acid amide according to 9.

* * * * *